US008420676B2

(12) United States Patent
Rhee et al.

(10) Patent No.: US 8,420,676 B2
(45) Date of Patent: *Apr. 16, 2013

(54) OXAZOLIDINONE DERIVATIVES

(75) Inventors: Jae Keol Rhee, Kyonggido (KR); Weon Bin Im, Yongin-si (KR); Chong Hwan Cho, Yongin-si (KR); Sung Hak Choi, Seongnam-si (KR); Tae Ho Lee, Yongin-si (KR)

(73) Assignee: Dong-A Pharmaceuticals Co. Ltd., Seoul (KR)

(*) Notice: Subject to any disclaimer, the term of this patent is extended or adjusted under 35 U.S.C. 154(b) by 1208 days.

This patent is subject to a terminal disclaimer.

(21) Appl. No.: 12/211,655

(22) Filed: Sep. 16, 2008

(65) Prior Publication Data

US 2009/0192197 A1 Jul. 30, 2009

Related U.S. Application Data

(62) Division of application No. 10/596,412, filed as application No. PCT/KR2004/003327 on Dec. 17, 2004, now Pat. No. 7,816,379.

(30) Foreign Application Priority Data

Dec. 18, 2003 (KR) ........................ 10-2003-0093342
Jul. 27, 2004 (KR) ........................ 10-2004-0058809

(51) Int. Cl.
*A61K 31/4439* (2006.01)
*C07D 413/14* (2006.01)

(52) U.S. Cl.
USPC ..................... 514/340; 546/268.1; 546/269.4

(58) Field of Classification Search ................ 546/269.4, 546/268.1; 514/340
See application file for complete search history.

(56) References Cited

U.S. PATENT DOCUMENTS

| | | | |
|---|---|---|---|
| 4,128,654 A | 12/1978 | Fugitt et al. | |
| 4,250,318 A | 2/1981 | Dostert et al. | |
| 4,340,606 A | 7/1982 | Fugitt et al. | |
| 4,461,773 A | 7/1984 | Gregory | |
| 4,476,136 A | 10/1984 | Dostert et al. | |
| 4,948,801 A | 8/1990 | Carlson et al. | |
| 5,523,403 A | 6/1996 | Barbachyn | |
| 5,565,571 A | 10/1996 | Barbachyn | |
| 5,652,238 A | 7/1997 | Brickner et al. | |
| 5,688,792 A | 11/1997 | Barbachyn et al. | |
| 6,689,779 B2 | 2/2004 | Lee et al. | |
| 7,129,259 B2 | 10/2006 | Chen et al. | |
| 7,141,583 B2 | 11/2006 | Gravestock et al. | |
| 7,144,911 B2 | 12/2006 | Flynn et al. | |
| 7,202,257 B2 | 4/2007 | Flynn et al. | |
| 7,396,847 B2 | 7/2008 | Gravestock et al. | |
| 7,462,633 B2 | 12/2008 | Fukuda | |
| 7,473,699 B2 | 1/2009 | Gravestock et al. | |
| 7,498,350 B2 | 3/2009 | Gravestock et al. | |
| 7,816,379 B2 | 10/2010 | Rhee et al. | |

| | | |
|---|---|---|
| 2002/0115669 A1 | 8/2002 | Wiedeman et al. |
| 2003/0166620 A1 | 9/2003 | Lee et al. |
| 2004/0180906 A1 | 9/2004 | Flynn et al. |
| 2005/0038092 A1 | 2/2005 | Fukuda |
| 2005/0107435 A1 | 5/2005 | Gravestock et al. |
| 2005/0288286 A1 | 12/2005 | Flynn et al. |
| 2006/0116386 A1 | 6/2006 | Gravestock |
| 2006/0116400 A1 | 6/2006 | Carcanague et al. |
| 2006/0270637 A1 | 11/2006 | Gravestock et al. |
| 2007/0155798 A1 | 7/2007 | Rhee et al. |
| 2007/0185132 A1 | 8/2007 | Fukuda |
| 2007/0191336 A1 | 8/2007 | Flynn et al. |
| 2007/0203187 A1 | 8/2007 | Fukuda |
| 2007/0208062 A1 | 9/2007 | Carcanague et al. |
| 2008/0021012 A1 | 1/2008 | Gravestock et al. |
| 2008/0021071 A1 | 1/2008 | Gravestock et al. |
| 2008/0064689 A1 | 3/2008 | Carcanague et al. |
| 2009/0018123 A1 | 1/2009 | Sindkhedkar et al. |
| 2009/0192197 A1 | 7/2009 | Rhee et al. |
| 2010/0093669 A1 | 4/2010 | Simson et al. |
| 2010/0227839 A1 | 9/2010 | Reichenbacher et al. |

FOREIGN PATENT DOCUMENTS

| | | |
|---|---|---|
| AU | 2004299413 | 7/2009 |
| AU | 2009200606 | 4/2011 |
| CA | 2 549 062 | 7/2011 |
| CN | 101982468 A | 3/2011 |
| EP | 0312000 | 4/1989 |
| EP | 0 352 781 | 1/1990 |
| EP | 1 699 784 | 9/2006 |
| EP | 2 305 657 | 4/2011 |
| IN | 236862 | 11/2009 |
| JP | A-S57-99576 | 6/1982 |
| NZ | 547928 | 9/2009 |
| NZ | 575842 | 2/2011 |
| WO | WO 93/09103 | 5/1993 |
| WO | WO 93/23384 | 11/1993 |
| WO | WO 95/07271 | 3/1995 |
| WO | WO 95/14684 | 6/1995 |
| WO | WO 01/94342 | 12/2001 |
| WO | WO 02/081470 | 10/2002 |
| WO | WO 03/022824 | 3/2003 |
| WO | WO 03/035648 | 5/2003 |

(Continued)

OTHER PUBLICATIONS

Ettmayer et al. "Lessons Learned from Marketed and Investigational Prodrugs." J. Med. Chem., (2004), 47(10): 2393-2404.*

(Continued)

*Primary Examiner* — Patricia L Morris
(74) *Attorney, Agent, or Firm* — Knobbe, Martens, Olson & Bear LLP

(57) ABSTRACT

The present invention relates to novel derivatives of oxazolidinone, a method thereof and pharmaceutical compositions comprising the derivatives for use in an antibiotic. The oxazolidinone derivatives of the present invention show inhibitory activity against a broad spectrum of bacteria and lower toxicity. The prodrugs, prepared by reacting the compound having hydroxyl group with amino acid or phosphate, have an excellent efficiency on solubility thereof against water. Further, the derivatives of the present invention may exert potent antibacterial activity versus various human and animal pathogens, including Gram-positive bacteria such as, Staphylococci, Enterococci and Streptococci anaerobic microorganisms such as *Bacteroides* and Clostridia, and acid-resistant microorganisms such as *Mycobacterium tuberculosis* and *Mycobacterium avium*. Accordingly, the compositions comprising the oxazolidinone are used in an antibiotic.

33 Claims, No Drawings

FOREIGN PATENT DOCUMENTS

| WO | WO 03/047358 | 6/2003 |
| --- | --- | --- |
| WO | WO 03/072575 | 9/2003 |
| WO | WO 03/072576 | 9/2003 |
| WO | WO 2004/048350 | 6/2004 |
| WO | WO 2005/005398 | 1/2005 |
| WO | WO 2005/116017 | 12/2005 |
| WO | WO 2006/038100 | 4/2006 |
| WO | WO 2007/138381 | 12/2007 |
| WO | WO 2010/042887 | 4/2010 |
| WO | WO 2010/091131 | 8/2010 |
| WO | WO 2010/138649 | 12/2010 |

OTHER PUBLICATIONS

Stella, Valentino. "Prodrugs as therapeutics." Expert Opin. Ther. Patents (2004), 14(3): 277-280.*
Testa, Bernard. "Prodrug research: futile or fertile?" Biochemical Pharmacology, 68 (2004): 2393-2404.*
Wolff et al. Burger's Medicinal Chemistry and Drug Discovery. 5th ed. vol. 1: Principles and Practice. pp. 949-982.*
Wolff et al. Burger's Medicinal Chemistry and Drug Discovery, 5$^{th}$ ed. vol. 1. pp. 949-982, 1997.*
Australian Examiner's First Report, dated Oct. 12, 2010, re App. No. 2009200606.
Bae, Soo K., et al. 2007 "High-performance liquid chromatographic analysis of DA-7867, a new oxazolidinone, in human plasma and urine and in rat tissue homogenates", Journal of Chromatography B, (2003), pp. 397-403.
CA Notice of Allowance re App. No. 2,549,062, dated Apr. 7, 2011.
CA Office Action re App. No. 2,549,062 dated Aug. 21, 2008.
CA Office Action re App. No. 2,549,062 dated Jan. 12, 2011.
CA Office Action re App. No. 2,549,062 dated Mar. 30, 2009.
CN Decision of Rejection re App. No. CN 200480037612.2 dated Jun. 26, 2009.
CN Office Action re App. No. CN 200480037612.2 dated Jan. 9, 2009.
EP Extended Search Report re EP App. No. 10 18 3967, dated Mar. 25, 2011.
EPO Examination Report re App. No. EP 04 80 8458 dated Apr. 30, 2010.
EPO Examination Report re App. No. EP 04 80 8458 dated Aug. 10, 2009.
EPO Supplemental Search Report re App. No. EP 04 80 8458 dated Jul. 24, 2008.
Hiroshi, Nagase ed. Medicinal Chemistry, Technomics, Sep. 25, 1999, The Second Volume, pp. 368-382.
International Partial Search Report re App. No. PCT/US2009/060267, dated Jan. 14, 2010.
International Preliminary Report on Patentability and Written Report, re PCT/US2009/060267 mailed on Apr. 21, 2011.
International Preliminary Report on Patentability for PCT/KR2004/003327 dated Jan. 9, 2006.
International Search Report and Written Opinion re App. No. PCT/US2009/060267, dated May 7, 2010.
International Search Report and Written Opinion re App. No. PCT/US2010/023122 dated Jul. 16, 2010.
International Search Report and Written Opinion re App. No. PCT/US2010/036283 dated Aug. 6, 2010.
International Search Report for PCT/KR2004/003327 dated Mar. 24, 2005.
Japanese Office Action re JP App. No. 2006-545238, dated Sep. 21, 2010.
Mexico Office Action re App. No. PA/a/2006/006955, dated Dec. 10, 2010.
NZ Examination Report re NZ Application No. 589161, dated Nov. 30, 2010.
NZ Office Action re App. No. 575842 dated Jan. 19, 2011.
NZ Office Action re App. No. 575842 dated Jul. 15, 2010.
NZ Office Action re App. No. 575842 dated Mar. 31, 2009.
NZ Office Action re App. No. 575842 dated Sep. 23, 2010.
NZ Office Action re App. No. 575842, dated Jul. 1, 2011.
Response to Office Action in Japanese Application No. 2006-545238 dated Apr. 4, 2011.
Bae, Soo K., et al. 2007 "Pharmacokinetics of DA-7218, a New Oxazolidinone, and Its Active Metabolite, DA-7157, After Intravenous and Oral Administration of DA-7218 and DA-7157 to Rats", Journal of Pharmacy and Pharmacology 59:955-963.
Prado-Prado, Francisco, J., et al. 2007 "Unified QSAR Approach to Antimicrobials. Part 2: Predicting Activity Against More Than 90 Different Species in Order to Halt Antibacterial Resistance", Bioorganic & Medicinal Chemistry, 15:897-902.
Rondestvedt, Christian, S., Jr., et al. 1955. "Unsaturated sulfonic acids. V", Journal of the American Chemical Society, 77:6532-6540.
Vera-Cabrera, Lucio, et al. 2006 "In Vitro Activities of DA-7157 and DA-7218 Against Mycobacterium Tuberculosis and Nocardia Brasiliensis", Antimicrobial Agents and Chemotherapy 50:3170-3172.
Vera-Cabrera, Lucio, et al. 2006 "In Vitro Activities of the Novel Oxazolidinones DA-7867 and DA-7157 Against Rapidly and Slowly Growing Mycobacteria", Antimicrobial Agents and Chemotherapy 50:4027-4029.
J. Med. Chem. 32, 1673 (1989).
J. Med. Chem. 33, 2569 (1990).
International Search Report issued in International Application No. PCT/GB 03/05091 on Aug. 15, 2004.
Supplementary European Search Report dated Jul. 31, 2008.
Tetrahedron, vol. 45 No. 5 pp. 1323-1326, 1989 "Chiral Synthesis of Dup 721, A New Antibacterial Agent1, Chia-Lin J. Wang, Walter A. Gregory, and Mark A. Wuonola E.I. Du Pont De Nemours and Company, Inc., Medical Products Department Pharh4aceutical Research and Development Division Experimental Station".

* cited by examiner

OXAZOLIDINONE DERIVATIVES

CROSS-REFERENCE TO RELATED APPLICATIONS

This application is a Divisional of U.S. patent application Ser. No. 10/596,412 filed on Jun. 13, 2006, now U.S. Pat. No. 7,816,379 which is a National Phase application of PCT/KR04/03327, filed on Dec. 17, 2004, which claims priority to KR102003-0093342 and KR102004-0058809, the full disclosure of each of these documents is incorporated by reference in their entirety herein.

BACKGROUND OF THE INVENTION

1. Technical Field

The present invention relates to novel derivatives of oxazolidinone, preparation methods of the same, and pharmaceutical compositions comprising the same for use in an antibiotic.

2. Description of the Related Art

Used as orally administrable antibacterial agents, oxazolidinone compounds are not products of fermentation, but artificially synthesized ones, and various structures of their derivatives are known. For instance, 3-phenyl-2-oxazolidinone derivatives having one or two substituents are stated in U.S. Pat. Nos. 4,948,801, 4,461,773, 4,340,606, 4,476,136, 4,250,318 and 4,128,654. 3-[(Monosubstituted) phenyl]-2-oxazolidinone derivatives of Formula 2 are disclosed in EP 0312000, J. Med. Chem. 32, 1673 (1989), J. Med. Chem. 33, 2569 (1990), Tetrahedron, 45, 123 (1989), etc.

Formula 2

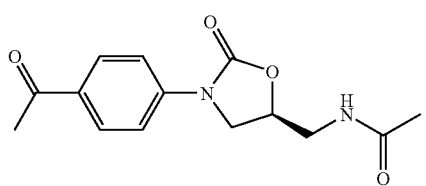

Pharmacia & Upjohn developed oxazolidinone derivatives of Formulas 3 and 4 (WO 93/23384, WO 95/14684 and WO 95/07271). Having succeeded in gaining the approval of the Food and Drug Administration (FDA) of U.S.A., the oxazolidinone derivative of Formula 3, by the name of 'Zyvox', has come into the market. However, these conventional synthetic oxazolidinone compounds were found to suffer from the disadvantage of showing antibacterial activity against a narrow spectrum of bacteria, being toxic to humans, and being poor in therapeutic activity in vivo. Zyvox may be used restrictively as injection since the solubility of Zyvox against water is inadequate for use in injection, which is about 3 mg/ml.

Formula 3

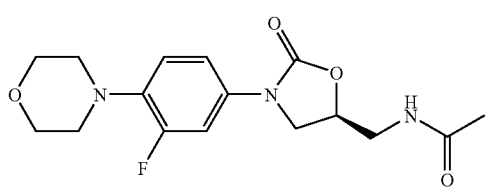

Formula 4

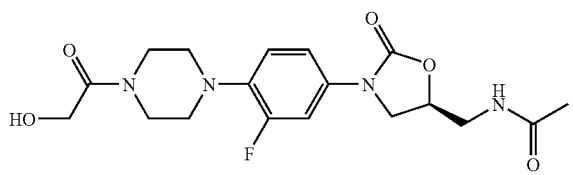

Further, WO 93/09103 discloses derivatives of phenyl oxazolidinone, substituted with heterocyclics such as thiazole, indole, oxazole and quinole, as well as pyridine, at position 4 of the phenyl ring. However, these derivatives of oxazolidinone are known as providing insufficient medicinal effects because the heterocyclics bear simple substituents such as alkyl or amino groups.

In WO 01/94342, synthesizing derivatives of phenyl oxazolidinone, having with pyridine or derivatives of phenyl at position 4 of the phenyl ring was described. The compounds synthesized are potent in inhibitory activity against a broad spectrum of bacteria and are also superior antibiotic to Zyvox. However, The compounds are unable to be formulated as injection because solubility of the same is under 30 μg/ml.

Accordingly, the intensive and thorough research on oxazolidinone derivatives, conducted by the present inventors aiming to overcome the above problems encountered in prior arts, resulted in the finding oxazolidinone derivatives as well as prodrugs thereof, wherein the prodrugs are prepared by reacting amino acid or phosphate with the oxazolidinone derivatives having hydroxyl group. Further, salts of the oxazolidinone derivatives prodruged were easily synthesized by using amine group of amino acid of the same to synthesize organic acid or inorganic acid and by using a hydroxyl group of phosphate and one selected from sodium and calcium. The oxazolidinone derivatives have excellent effects on antibiotic activity and the solubility of the same is greatly enhanced.

SUMMARY OF THE INVENTION

Disclosure of the Invention

Technical Problem

It is an object of the present invention to provide novel derivatives of oxazolidinone.

It is another object of the present invention to provide a method of preparing the above-mentioned derivatives.

It is still another object of the present invention to provide a pharmaceutical composition comprising the above-mentioned derivatives for use in an antibiotic.

Technical Solution

The present invention provides novel derivatives of oxazolidinone corresponding to Formula 1 defined below.

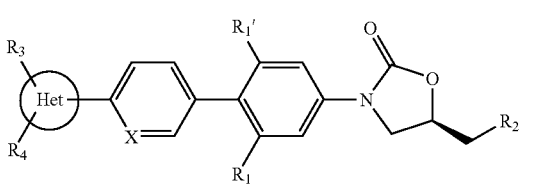

Formula 1

In the Formula 1, X represents carbon or nitrogen.

$R_1$ and $R_1'$ respectively represent hydrogen or fluorine.

$R_2$ represents —$NR_5R_6$, —$OR_7$, triazol, fluorine, alkylphosphate, monophosphate or a metal salt of phosphate;

$R_5$ and $R_6$, which are the same or different, respectively represent hydrogen, C. sub. 1-4 alkyl group or acetyl; and $R_7$ is hydrogen, C. sub. 1-3 alkyl group or acylated amino acid. When the $R_7$ is acylated amino acid, amino acid refers to alanine, glycine, proline, isoleucine, leucine, phenylalanine, β-alanine or valine.

Het, which is a heterocyclic ring or a hetero aromatic ring, refers to pyrrole, furan, piperazine, piperidine, imidazole, 1,2,4-triazol, 1,2,3-triazol, tetrazole, pyrazole, pyrrolidine, oxazole, isoxazole, oxadiazole, pyridin, pyrimidine, thiazole or pyrazine.

$R_3$ and $R_4$, which are the same or different, respectively refer to hydrogen, C. sub. 1-4 alkyl group that is substituted or unsubstituted with cyano, —$(CH_2)_m$—$OR_7$ (m represents 0, 1, 2, 3, 4) or ketone.

The derivatives of oxazolidinone corresponding to Formula 1 may be used for a pharmaceutically acceptable salt, it is preferably an acid addition salt prepared by using pharmaceutically acceptable free acid. The free acid may be inorganic or organic. The inorganic free acid may comprise hydrochloric acid, bromic acid, sulfuric acid, phosphoric acid, etc. The organic free acid may include citric acid, acetic acid, lactic acid, maleic acid, fumaric acid, gluconic acid, methane sulfonic acid, glyconic acid, succinic acid, 4-toluenesulfonic acid, trifluoroacetic acid, galuturonic acid, embonic acid, glutamic acid, aspartic acid, etc.

Preferred compounds of the oxazolidinone derivatives according to the present invention include the following compounds and their structures are described in Table 1.

1) (S)-3-(4-(2-(2-oxo-4-glycyloxymethylpylolidin-1-yl)pyridin-5-yl)-3-fluorophenyl)-2-oxo-5-oxazolidinylmethyl acetamide trifluoroacetic acid,
2) (S)-3-(4-(2-(4-glycyloxymethyl-1,2,3-triazol-1-yl)pyridin-5-yl)-3-fluorophenyl)-2-oxo-5-oxazolidinylmethyl acetamide trifluoroacetic acid,
3) (S)-3-(4-(2-(5-glycyloxymethylisoxazol-3-yl)pyridin-5-yl)-3-fluorophenyl)-2-oxo-5-oxazolidinylmethyl acetamide trifluoroacetic acid,
4) (R)-3-(4-(2-(2-methyltetrazol-5-yl)pyridin-5-yl)-3-fluorophenyl)-5-([1,2,4]triazol-1-yl)methyl oxazolidin-2-one,
5) (S)-3-(4-(2-(2-oxo-3-glycyloxypyrrolidine-1-yl)pyridin-5-yl)-3-fluorophenyl)-2-oxo-5-oxazolidinylmethyl acetamide trifluoroacetic acid,
6) (S)-3-(4-(2-(5-glycyloxymethyl-[1,2,4]oxadiazole-3-yl)pyridin-5-yl)-3-fluorophenyl)-2-oxo-5-oxazolidinylmethyl acetamide trifluoroacetic acid,
7) (S)-3-(4-(2-(5-glycyloxymethyl-4,5-dihydroisoxazole-3-yl)pyridin-5-yl)-3-fluorophenyl)-2-oxo-5-oxazolidinylmethyl acetamide trifluoroacetic acid,
8) (R)-3-(4-(2-(2-methyltetrazol-5-yl)pyridin-5-yl)-3-fluorophenyl)-5-([1,2,3]triazol-2-yl)methyl oxazolidin-2-one,
9) (R)-3-(4-(2-(2-methyltetrazol-5-yl)pyridin-5-yl)-3-fluorophenyl)-5-([1,2,3]triazol-1-yl)methyl oxazolidin-2-one,
10) (R)-3-(4-(2-(2-methyltetrazol-5-yl)pyridin-5-yl)-3-fluorophenyl)-5-hydroxymethyl oxazolidin-2-one,
11) (S)-3-(4-(4-(4,5-dimethyloxazol-2-yl)phenyl)-3-fluorophenyl)-2-oxo-5-oxazolidinylmethyl acetamide,
12) (R)-3-(4-(2-(2-methyltetrazol-5-yl)pyridin-5-yl)-3-fluorophenyl)-5-glycyloxymethyl oxazolidin-2-one trifluoroacetic acid,
13) (R)-3-(4-(2-(2-methyl-[1,3,4]oxadiazol-5-yl)pyridin-5-yl)-3-fluorophenyl)-5-([1,2,3]triazol-1-yl)methyl oxazolidin-2-one,
14) (R)-3-(4-(2-([1,2,4]triazol-1-yl)pyridin-5-yl)-3-fluorophenyl)-5-([1,2,3]triazol-1-yl)methyl oxazolidin-2-one,
15) (S)-3-(4-(2-(4,5-dimethyloxazol-2-yl)pyridin-5-yl)-3-fluorophenyl)-2-oxo-5-oxazolidinyl]methyl acetamide,
16) (R)-3-(4-(2-(2-methyl-[1,3,4]oxadiazol-5-yl)pyridin-5-yl)-3-fluorophenyl)-5-hydroxymethyl oxazolidin-2-one,
17) (R)-3-(4-(2-[1,2,4]triazol-1-yl pyridin-5-yl)-3-fluorophenyl)-5-hydroxymethyl oxazolidin-2-one,
18) (R)-3-(4-(2-(2-methyltetrazol-5-yl)pyridin-5-yl)-3-fluorophenyl)-5-fluoromethyl oxazolidin-2-one,
19) (S)-3-(4-(2-(imidazole-1-yl)pyridin-5-yl)-3-fluorophenyl)-5-aminomethyl oxazolidin-2-one hydrochloride,
20) (R)-3-(4-(2-(2-methyltetrazol-5-yl)pyridin-5-yl)-3-fluorophenyl)-5-(L-valyloxy)methyl oxazolidin-2-one trifluoroacetic acid,
21) (R)-3-(4-(4-(4,5-dimethyloxazol-2-yl)phenyl)-3-fluorophenyl)-5-hydroxymethyl oxazolidin-2-one,
22) (R)-3-(4-(2-([1,2,3]triazol-1-yl)pyridin-5-yl)-3-fluorophenyl)-5-glycyloxymethyl oxazolidin-2-one trifluoroacetic acid,
23) (R)-3-(4-(4-(4,5-dimethyloxazol-2-yl)phenyl)-3-fluorophenyl)-5-glycyloxymethyl oxazolidin-2-one trifluoroacetic acid,
24) (R)-3-(4-(2-([1,2,3]triazol-1-yl)pyridin-5-yl)-3-fluorophenyl)-5-hydroxymethyl oxazolidin-2-one,
25) (S)-3-(4-(2-([1,2,3]triazol-2-yl)pyridin-5-yl)-3-fluorophenyl)-2-oxo-5-oxazolidinylmethyl acetamide,
26) (S)-3-(4-(4-(4(S)-hydroxymethyl-4,5-dihydroxazole-2-yl)phenyl)-3-fluorophenyl)-2-oxo-5-oxazolidinylmethyl acetamide,
27) (R)-3-(4-(2-(2-methyl-[1,3,4]oxadiazole-5-yl)pyridin-5-yl)-3-fluorophenyl)-5-glycyloxymethyl oxazolidin-2-one trifluoroacetic acid,
28) (S)-3-(4-(4-(4-hydroxymethylthiazol-2-yl)phenyl)-3-fluorophenyl)-2-oxo-5-oxazolidinylmethyl acetamide,
29) (R)-3-(4-(2-([1,2,3]triazol-2-yl)pyridin-5-yl)-3-fluorophenyl)-5-hydroxymethyl oxazolidin-2-one,
30) (S)-3-(4-(4-(4-glycyloxymethylthiazol-2-yl)phenyl)-3-fluorophenyl)-2-oxo-5-oxazolidinylmethyl acetamide trifluoroacetic acid,
31) (S)-3-(4-(4-(4-cyanomethyl thiazol-2-yl)phenyl)-3-fluorophenyl)-2-oxo-5-oxazolidinylmethyl acetamide,
32) (R)-3-(4-(4-(4-cyanomethyl thiazol-2-yl)phenyl)-3-fluorophenyl)-5-hydroxymethyl oxazolidin-2-one,
33) (R)-3-(4-(2-(2-methyltetrazol-5-yl)pyridin-5-yl)-3-fluorophenyl)-5-methoxymethyl oxazolidin-2-one,
34) (R)-3-(4-(4-(4-cyanomethyl thiazol-2-yl)phenyl)-3-fluorophenyl)-5-glycyloxymethyl oxazolidin-2-one trifluoroacetic acid,
35) (R)-3-(4-(2-([1,2,3]triazol-2-yl)pyridin-5-yl)-3-fluorophenyl)-5-glycyloxymethyl oxazolidin-2-one trifluoroacetic acid,
36) (R)-3-(4-(4-(4-hydroxymethyl thiazol-2-yl)phenyl)-3-fluorophenyl)-5-([1,2,3]triazol-1-yl)methyl oxazolidin-2-one, 37) (R)-3-(4-(4-(4-glycyloxymethyl thiazol-2-yl)phenyl)-3-fluorophenyl)-5-([1,2,3]triazol-1-yl)methyl oxazolidin-2-one trifluoroacetic acid,
38) (R)-3-(4-(2-(2-methyltetrazol-5-yl)pyridin-5-yl)-3,5-difluorophenyl)-5-hydroxymethyl oxazolidin-2-one,
39) (R)-3-(4-(2-(2-methyl-[1,3,4]oxadiazol-5-yl)pyridin-5-yl)-3,5-difluorophenyl)-5-hydroxymethyl oxazolidin-2-one,
40) (R)-3-(4-(2-(2-methyltetrazol-5-yl)pyridin-5-yl)-3-fluorophenyl)-5-(N,N-dimethylaminomethyl)oxazolidin-2-one,
41) (R)-3-(4-(2-(2-methyltetrazol-5-yl)pyridin-5-yl)-3-fluorophenyl)-5-(N-methylaminomethyl)oxazolidin-2-one,
42) (R)-3-(4-(2-(2-methyltetrazol-5-yl)pyridin-5-yl)-3-fluorophenyl)-5-(L-alanyloxy)methyl oxazolidin-2-one trifluoroacetic acid,
43) (R)-3-(4-(2-(2-methyltetrazol-5-yl)pyridin-5-yl)-3-fluorophenyl)-5-(L-valyloxy)methyl oxazolidin-2-one hydrochloride,
44) (R)-3-(4-(2-(2-methyltetrazol-5-yl)pyridin-5-yl)-3-fluorophenyl)-5-(L-alanyloxy)methyl oxazolidin-2-one hydrochloride,
45) (R)-3-(4-(2-(2-methyltetrazol-5-yl)pyridin-5-yl)-3-fluorophenyl)-5-glycyloxymethyl oxazolidin-2-one hydrochloride,
46) (R)-3-(4-(2-(2-methyltetrazol-5-yl)pyridin-5-yl)-3-fluorophenyl)-5-(L-prolinyloxy)methyl oxazolidin-2-one trifluoroacetic acid,
47) (R)-3-(4-(2-(2-methyltetrazol-5-yl)pyridin-5-yl)-3-fluorophenyl)-5-(L-prolinyloxy)methyl oxazolidin-2-one hydrochloride,
48) (R)-3-(4-(2-(2-methyl-[1,3,4]oxadiazol-5-yl)pyridin-5-yl)-3-fluorophenyl)-5-glycyloxymethyl oxazolidin-2-one hydrochloride,
49) (R)-3-(4-(2-(2-methyltetrazol-5-yl)pyridin-5-yl)-3-fluorophenyl)-5-(β-alanyloxy)methyl oxazolidin-2-one trifluoroacetic acid,
50) (R)-3-(4-(2-(2-methyltetrazol-5-yl)pyridin-5-yl)-3-fluorophenyl)-5-(β-alanyloxy)methyl oxazolidin-2-one hydrochloride,
51) (R)-3-(4-(2-(2-methyl-[1,3,4]oxadiazol-5-yl)pyridin-5-yl)-3-fluorophenyl)-5-(L-alanyloxy)methyl oxazolidin-2-one trifluoroacetic acid,
52) (R)-3-(4-(2-(2-methyl-[1,3,4]oxadiazol-5-yl)pyridin-5-yl)-3-fluorophenyl)-5-(L-alanyloxy)methyl oxazolidin-2-one hydrochloride,
53) (R)-3-(4-(2-(2-methyl-[1,3,4]oxadiazol-5-yl)pyridin-5-yl)-3-fluorophenyl)-5-(L-valyloxy)methyl oxazolidin-2-one trifluoroacetic acid,
54) (R)-3-(4-(2-(2-methyl-[1,3,4]oxadiazol-5-yl)pyridin-5-yl)-3-fluorophenyl)-5-(L-valyloxy)methyl oxazolidin-2-one hydrochloride,
55) (R)-3-(4-(2-(2-methyl-[1,3,4]oxadiazol-5-yl)pyridin-5-yl)-3-fluorophenyl)-5-(L-prolinyloxy)methyl oxazolidin-2-one trifluoroacetic acid,
56) (R)-3-(4-(2-(2-methyl-[1,3,4]oxadiazol-5-yl)pyridin-5-yl)-3-fluorophenyl)-5-(L-prolinyloxy)methyl oxazolidin-2-one hydrochloride,
57) (R)-3-(4-(2-(2-methyl-[1,3,4]oxadiazol-5-yl)pyridin-5-yl)-3-fluorophenyl)-5-(β-alanyloxy)methyl oxazolidin-2-one trifluoroacetic acid,
58) (R)-3-(4-(2-(2-methyl-[1,3,4]oxadiazol-5-yl)pyridin-5-yl)-3-fluorophenyl)-5-(β-alanyloxy)methyl oxazolidin-2-one hydrochloride,
59) (R)-[3-(4-(2-(2-methyltetrazol-5-yl)pyridin-5-yl)-3-fluorophenyl)-2-oxo-5-oxazolidinyl]methyl disodiumphosphate,
60) (R)-[3-(4-(2-(2-methyl-[1,3,4]oxadiazol-5-yl)pyridin-5-yl)-3-fluorophenyl)-2-oxo-5-oxazolidinyl]methyl disodiumphosphate,
61) (R)-3-(4-(2-(1-methyltetrazol-5-yl)pyridin-5-yl)-3-fluorophenyl)-5-hydroxymethyl oxazolidin-2-one,
62) (R)-3-(4-(2-(1-methyltetrazol-5-yl)pyridin-5-yl)-3-fluorophenyl)-5-glycyloxymethyl oxazolidin-2-one trifluoroacetic acid,
63) (R)-3-(4-(2-(1-methyltetrazol-5-yl)pyridin-5-yl)-3-fluorophenyl)-5-glycyloxymethyl oxazolidin-2-one hydrochloride,
64) (R)-3-(4-(2-(1-methyltetrazol-5-yl)pyridin-5-yl)-3-fluorophenyl)-5-(L-alanyloxy)methyl oxazolidin-2-one trifluoroacetic acid,
65) (R)-3-(4-(2-(1-methyltetrazol-5-yl)pyridin-5-yl)-3-fluorophenyl)-5-(L-alanyloxy)methyl oxazolidin-2-one hydrochloride,
66) (R)-3-(4-(2-(1-methyltetrazol-5-yl)pyridin-5-yl)-3-fluorophenyl)-5-(L-valyloxy)methyl oxazolidin-2-one trifluoroacetic acid,
67) (R)-3-(4-(2-(1-methyltetrazol-5-yl)pyridin-5-yl)-3-fluorophenyl)-5-(L-valyloxy)methyl oxazolidin-2-one hydrochloride,
68) (R)-3-(4-(2-(1-methyltetrazol-5-yl)pyridin-5-yl)-3-fluorophenyl)-5-(β-alanyloxy)methyl oxazolidin-2-one trifluoroacetic acid,
69) (R)-3-(4-(2-(1-methyltetrazol-5-yl)pyridin-5-yl)-3-fluorophenyl)-5-(β-alanyloxy)methyl oxazolidin-2-one hydrochloride,
70) (R)-[3-(4-(2-(1-methyltetrazol-5-yl)pyridin-5-yl)-3-fluorophenyl)-2-oxo-5-oxazolidinyl]methyl disodiumphosphate,
71) (R)-3-(4-(2-(1-methyltetrazol-5-yl)pyridin-5-yl)-3-fluorophenyl)-5-([1,2,3]triazol-1-yl)methyl oxazolidin-2-one,
72) mono-[(R)-[3-(4-(2-(2-methyltetrazol-5-yl)pyridin-5-yl)-3-fluorophenyl)-2-oxo-5-oxazolidinyl]methyl]phosphate, and
73) mono-[(R)-[3-(4-(2-(1-methyltetrazol-5-yl)pyridin-5-yl)-3-fluorophenyl)-2-oxo-5-oxazolidinyl]methyl]phosphate.

TABLE 1

| Compound | Structure |
|---|---|
| 1 | 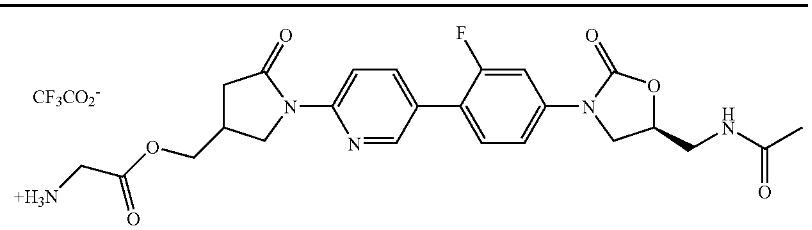 |

TABLE 1-continued

| Compound | Structure |
|---|---|
| 2 | 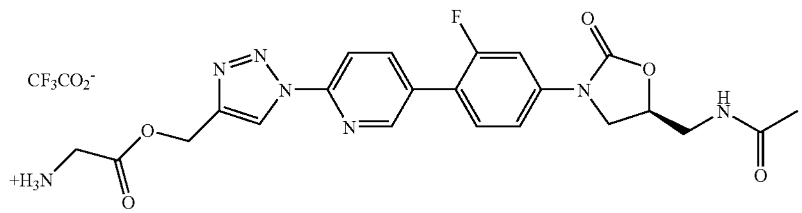 [SMILES: "CF3CO2-" ; CC(=O)NC[C@H]1CN(c2ccc(-c3ccc(-n4cc(COC(=O)C[NH3+])nn4)nc3)c(F)c2)C(=O)O1] |
| 3 | 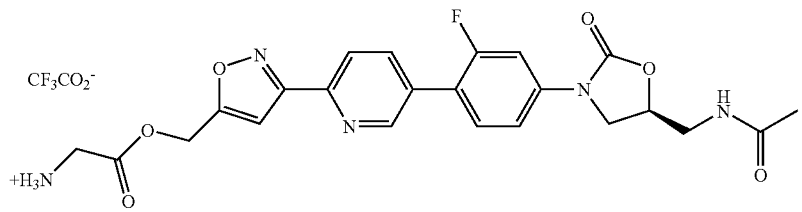 [SMILES: "CF3CO2-" ; CC(=O)NC[C@H]1CN(c2ccc(-c3ccc(-c4cc(COC(=O)C[NH3+])on4)nc3)c(F)c2)C(=O)O1] |
| 4 | 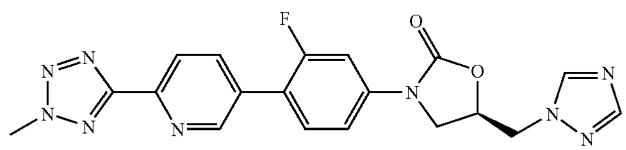 [SMILES: Cn1nnc(-c2ccc(-c3ccc(N4C[C@H](Cn5cncn5)OC4=O)cc3F)cn2)n1] |
| 5 | 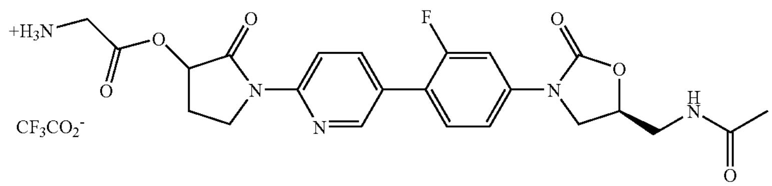 [SMILES: "CF3CO2-" ; CC(=O)NC[C@H]1CN(c2ccc(-c3ccc(N4CCC(OC(=O)C[NH3+])C4=O)nc3)c(F)c2)C(=O)O1] |
| 6 | 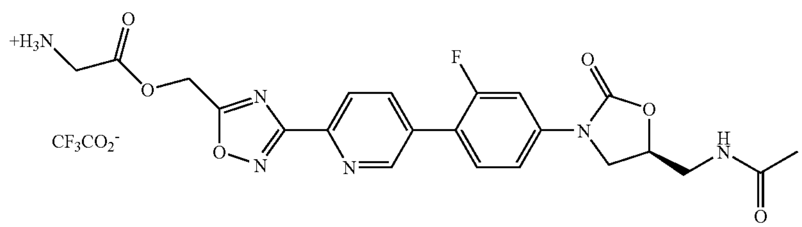 [SMILES: "CF3CO2-" ; CC(=O)NC[C@H]1CN(c2ccc(-c3ccc(-c4noc(COC(=O)C[NH3+])n4)nc3)c(F)c2)C(=O)O1] |
| 7 | 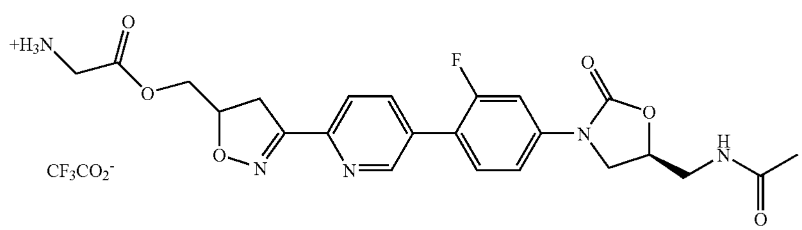 [SMILES: "CF3CO2-" ; CC(=O)NC[C@H]1CN(c2ccc(-c3ccc(C4=NOC(COC(=O)C[NH3+])C4)nc3)c(F)c2)C(=O)O1] |
| 8 | 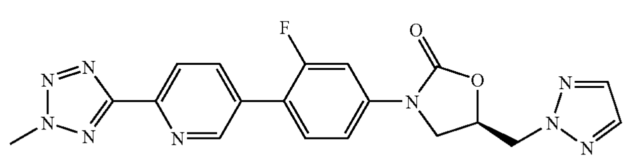 [SMILES: Cn1nnc(-c2ccc(-c3ccc(N4C[C@H](Cn5nccn5)OC4=O)cc3F)cn2)n1] |
| 9 | 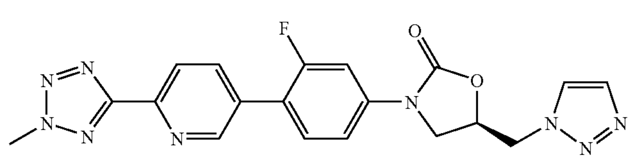 [SMILES: Cn1nnc(-c2ccc(-c3ccc(N4C[C@H](Cn5ccnn5)OC4=O)cc3F)cn2)n1] |

TABLE 1-continued

| Compound | Structure |
|---|---|
| 10 | 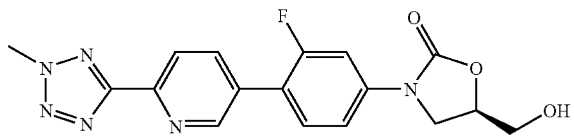 [SMILES: Cn1nnc(-c2ccc(-c3ccc(N4C[C@H](CO)OC4=O)cc3F)cn2)n1] |
| 11 | 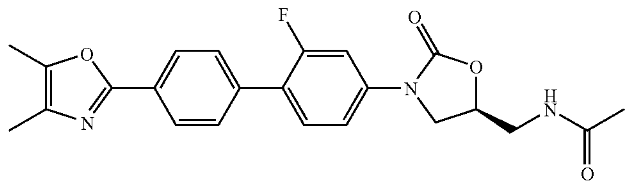 [SMILES: CC(=O)NC[C@H]1CN(c2ccc(-c3ccc(-c4nc(C)c(C)o4)cc3)c(F)c2)C(=O)O1] |
| 12 | 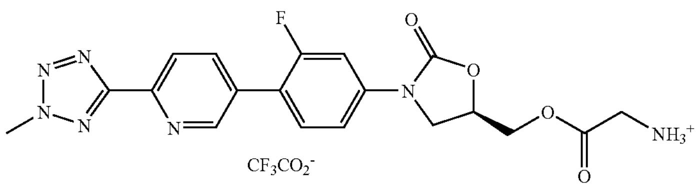 |
| 13 | 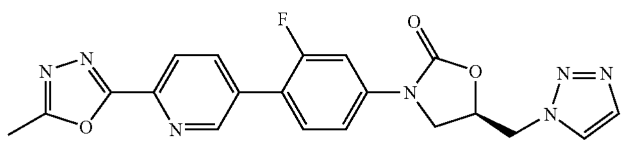 [SMILES: Cc1nnc(-c2ccc(-c3ccc(N4C[C@H](Cn5ccnn5)OC4=O)cc3F)cn2)o1] |
| 14 | 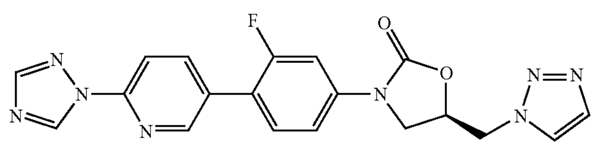 [SMILES: O=C1O[C@@H](Cn2ccnn2)CN1c1ccc(-c2ccc(-n3cncn3)nc2)c(F)c1] |
| 15 | 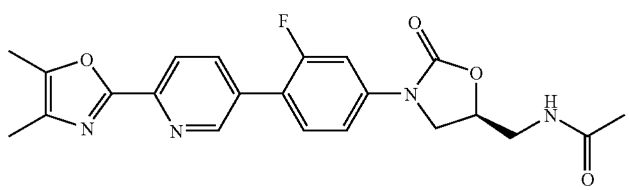 [SMILES: CC(=O)NC[C@H]1CN(c2ccc(-c3ccc(-c4nc(C)c(C)o4)nc3)c(F)c2)C(=O)O1] |
| 16 | 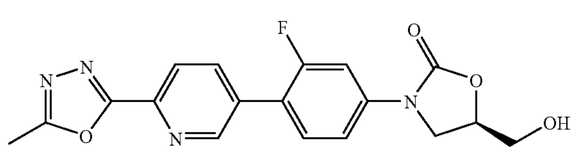 [SMILES: Cc1nnc(-c2ccc(-c3ccc(N4C[C@H](CO)OC4=O)cc3F)cn2)o1] |
| 17 | 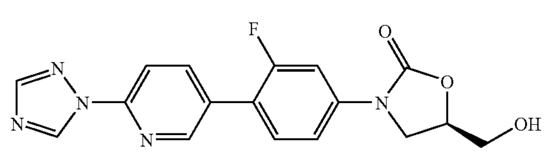 |
| 18 | 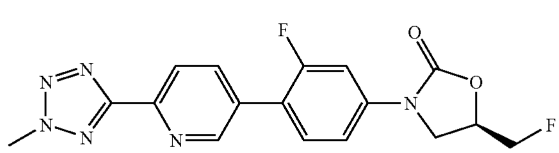 [SMILES: Cn1nnc(-c2ccc(-c3ccc(N4C[C@H](CF)OC4=O)cc3F)cn2)n1] |

TABLE 1-continued

| Compound | Structure |
| --- | --- |
| 19 | (imidazol-1-yl-pyridine)-(fluorophenyl)-oxazolidinone-CH₂NH₂·HCl |
| 20 | (2-methyltetrazol-5-yl-pyridine)-(fluorophenyl)-oxazolidinone-CH₂-O-C(O)-CH(NH₃⁺)-CH(CH₃)₂, CF₃CO₂⁻ |
| 21 | (4,5-dimethyloxazol-2-yl-phenyl)-(fluorophenyl)-oxazolidinone-CH₂OH |
| 22 | (1,2,3-triazol-1-yl-pyridine)-(fluorophenyl)-oxazolidinone-CH₂-O-C(O)-CH₂-NH₃⁺, CF₃CO₂⁻ |
| 23 | (4,5-dimethyloxazol-2-yl-phenyl)-(fluorophenyl)-oxazolidinone-CH₂-O-C(O)-CH₂-NH₃⁺, CF₃CO₂⁻ |
| 24 | (1,2,3-triazol-1-yl-pyridine)-(fluorophenyl)-oxazolidinone-CH₂OH |
| 25 | (1,2,3-triazol-2-yl-pyridine)-(fluorophenyl)-oxazolidinone-CH₂-NHAc |
| 26 | (4-hydroxymethyl-oxazolin-2-yl-phenyl)-(fluorophenyl)-oxazolidinone-CH₂-NHAc |

TABLE 1-continued

| Compound | Structure |
|---|---|
| 27 | 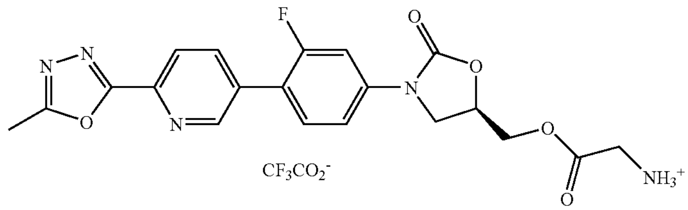 |
| 28 | 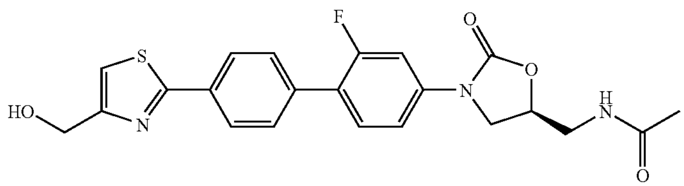 |
| 29 | 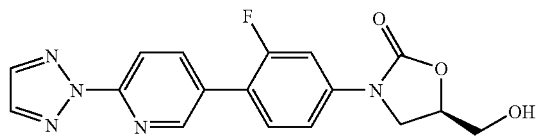 [SMILES: O=C1O[C@@H](CO)CN1c1ccc(-c2ccc(-n3nccn3)nc2)c(F)c1] |
| 30 | 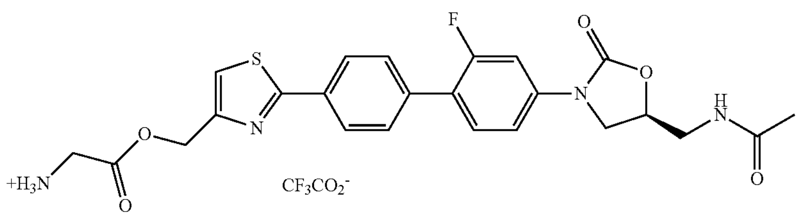 |
| 31 | 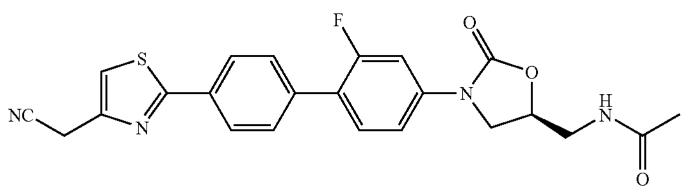 |
| 32 | 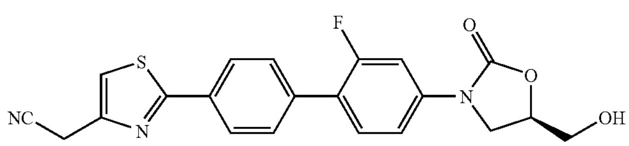 |
| 33 | 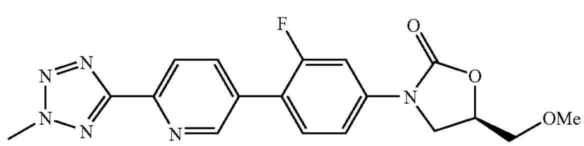 [SMILES: COC[C@H]1CN(c2ccc(-c3ccc(-c4nnn(C)n4)nc3)c(F)c2)C(=O)O1] |
| 34 | 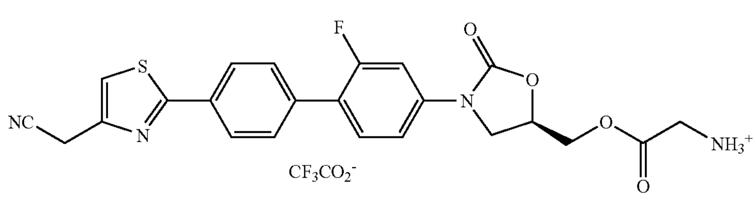 |

TABLE 1-continued

| Compound | Structure |
|---|---|
| 35 | 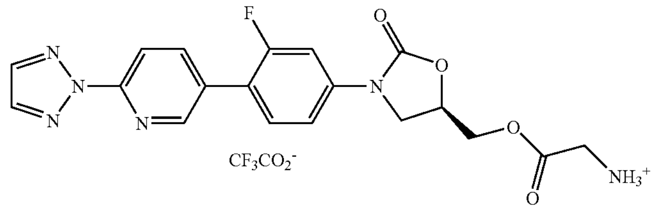 |
| 36 | 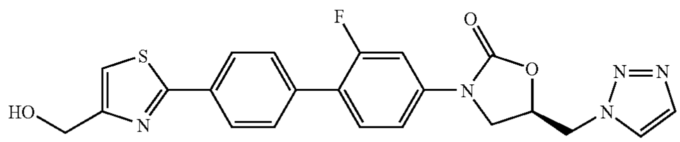 [SMILES: O=C1O[C@@H](Cn2ccnn2)CN1c1ccc(-c2ccc(-c3nc(CO)cs3)cc2)c(F)c1] |
| 37 | 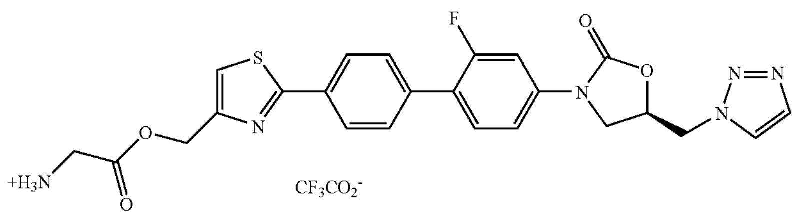 |
| 38 | 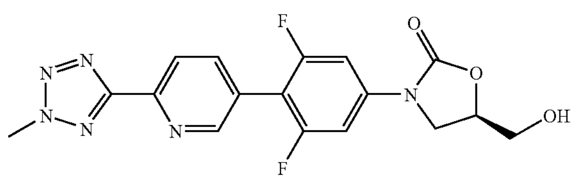 [SMILES: Cn1nnc(-c2ccc(-c3c(F)cc(N4C[C@H](CO)OC4=O)cc3F)cn2)n1] |
| 39 | 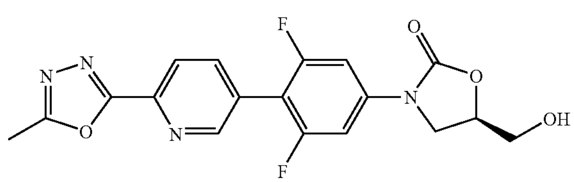 [SMILES: Cc1nnc(-c2ccc(-c3c(F)cc(N4C[C@H](CO)OC4=O)cc3F)cn2)o1] |
| 40 | 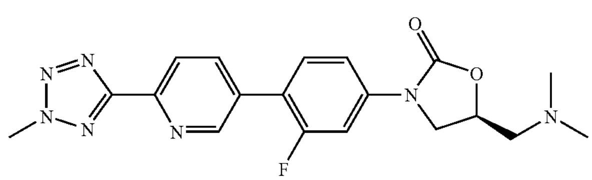 |
| 41 | 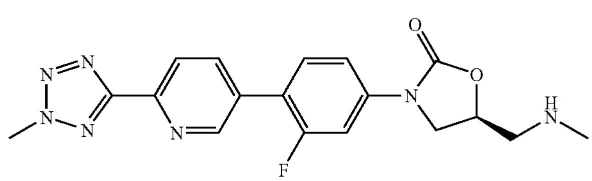 |
| 42 | 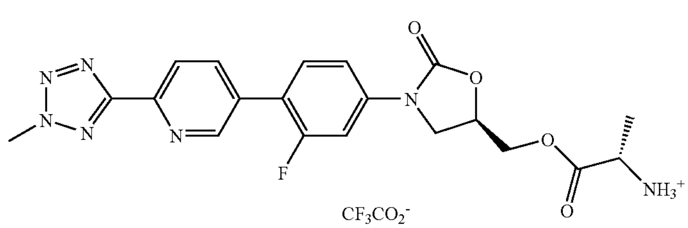 |

TABLE 1-continued

| Compound | Structure |
|---|---|
| 43 | 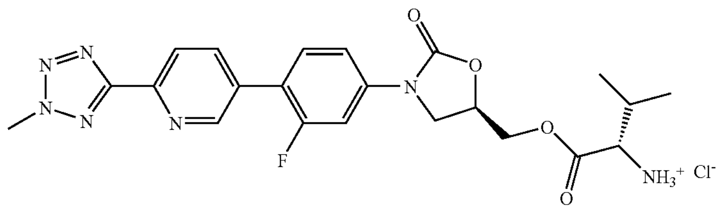 [SMILES: CC(C)[C@H]([NH3+])C(=O)OC[C@H]1CN(c2ccc(-c3ccc(-c4nnn(C)n4)nc3)c(F)c2)C(=O)O1 ; [Cl-]] |
| 44 | 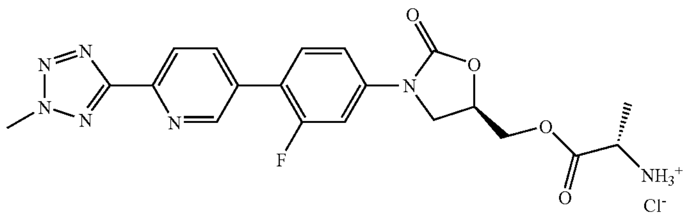 [SMILES: C[C@H]([NH3+])C(=O)OC[C@H]1CN(c2ccc(-c3ccc(-c4nnn(C)n4)nc3)c(F)c2)C(=O)O1 ; [Cl-]] |
| 45 | 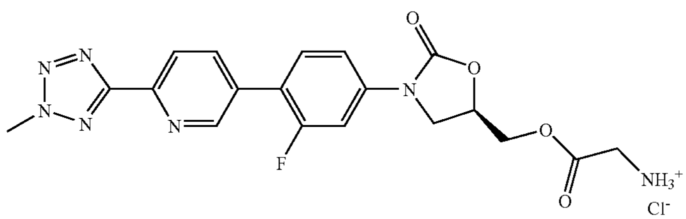 [SMILES: Cn1nnc(-c2ccc(-c3ccc(N4C[C@H](COC(=O)C[NH3+])OC4=O)cc3F)cn2)n1 ; [Cl-]] |
| 46 | 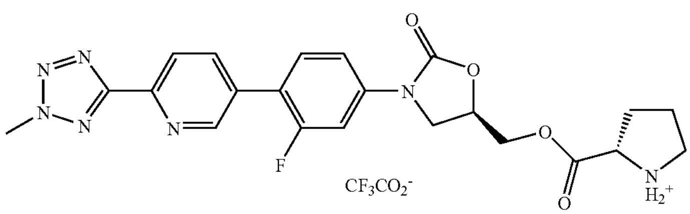 |
| 47 | 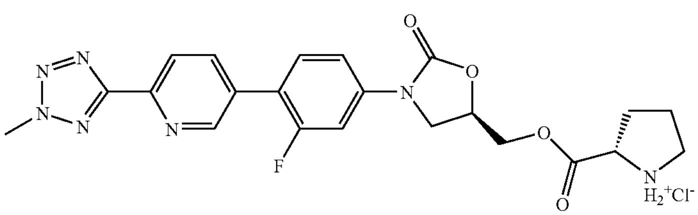 |
| 48 | 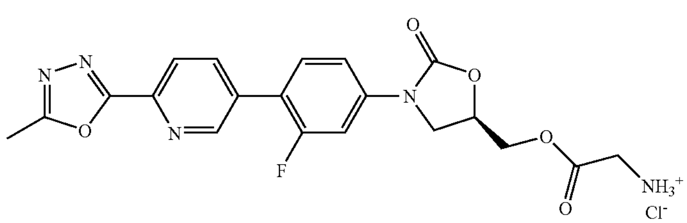 [SMILES: Cc1nnc(-c2ccc(-c3ccc(N4C[C@H](COC(=O)C[NH3+])OC4=O)cc3F)cn2)o1 ; [Cl-]] |
| 49 | 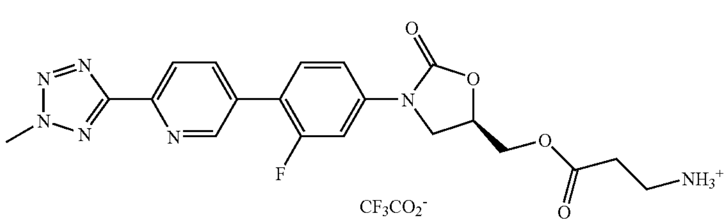 |

TABLE 1-continued
| Compound | Structure |
|---|---|
| 50 | 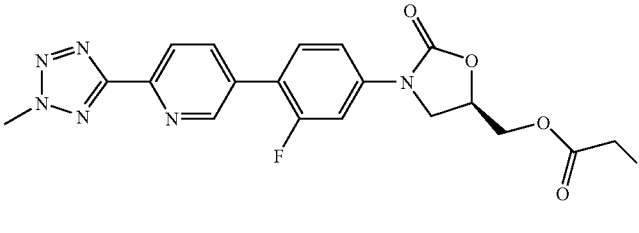 |
| 51 | 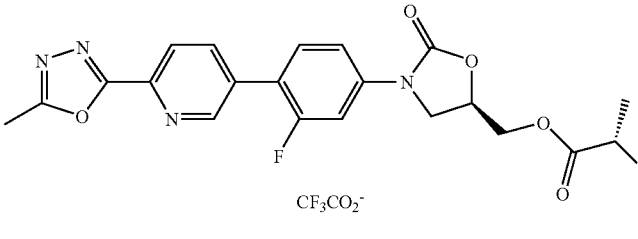 |
| 52 | 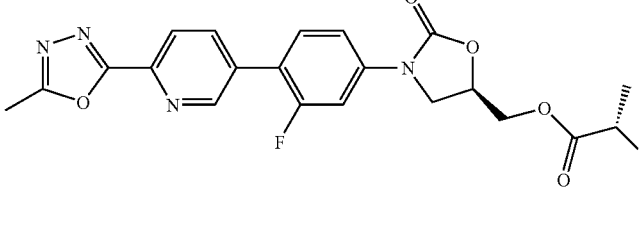 |
| 53 | 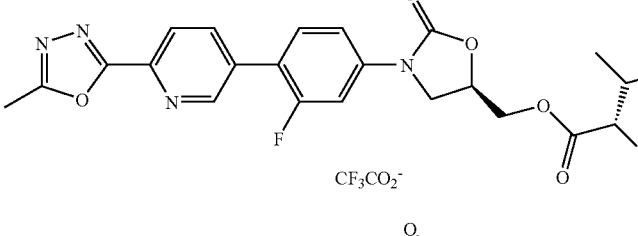 |
| 54 | 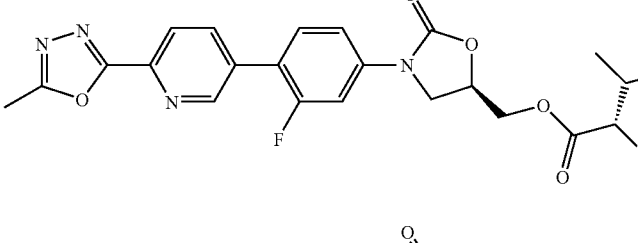 |
| 55 | 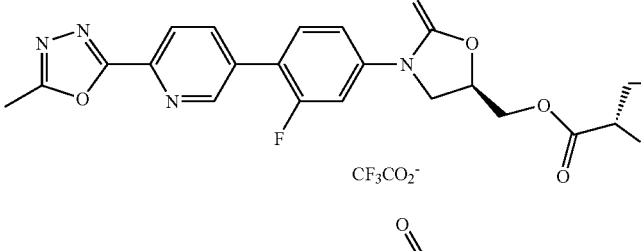 |
| 56 | 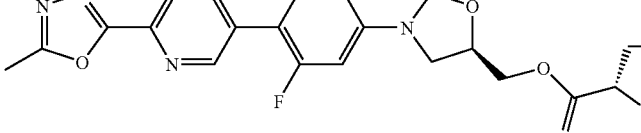 |

TABLE 1-continued

| Compound | Structure |
|---|---|
| 57 | [Structure: 5-methyl-1,3,4-oxadiazole-pyridine-fluorophenyl-oxazolidinone-CH2-O-C(O)-CH2CH2-NH3+ CF3CO2−] |
| 58 | [Structure: 5-methyl-1,3,4-oxadiazole-pyridine-fluorophenyl-oxazolidinone-CH2-O-C(O)-CH2CH2-NH3+ Cl−] |
| 59 | [Structure: 2-methyl-tetrazole-pyridine-fluorophenyl-oxazolidinone-CH2-O-P(O)(ONa)2] |
| 60 | [Structure: 5-methyl-1,3,4-oxadiazole-pyridine-fluorophenyl-oxazolidinone-CH2-O-P(O)(ONa)2] |
| 61 | [Structure: 1-methyl-tetrazole-pyridine-fluorophenyl-oxazolidinone-CH2-OH] |
| 62 | [Structure: 1-methyl-tetrazole-pyridine-fluorophenyl-oxazolidinone-CH2-O-C(O)-CH2-NH3+ CF3CO2−] |
| 63 | [Structure: 1-methyl-tetrazole-pyridine-fluorophenyl-oxazolidinone-CH2-O-C(O)-CH2-NH3+ Cl−] |

TABLE 1-continued

| Compound | Structure |
|---|---|
| 64 | (structure) |
| 65 | (structure) |
| 66 | (structure) |
| 67 | (structure) |
| 68 | (structure) |
| 69 | (structure) |
| 70 | (structure) |

TABLE 1-continued

| Compound | Structure |
|---|---|
| 71 | 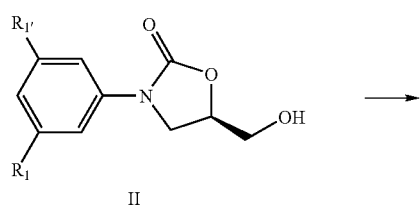 |
| 72 | 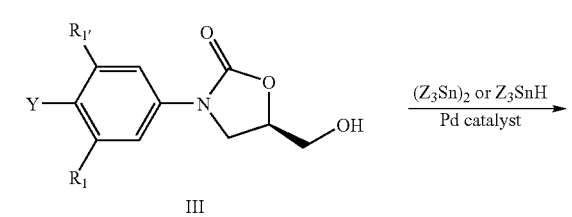 |
| 73 | 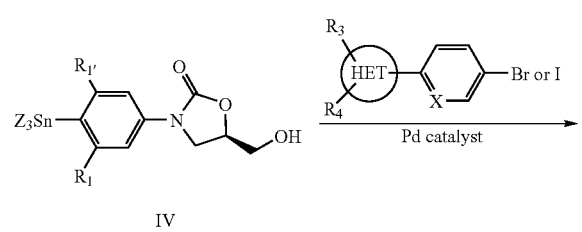 |

In Table 1, 'Ac' represents acetyl and 'TfOH' refers to trifluoroacetic acid.

Further, the present invention provides a method of preparing the derivatives of oxazolidinone corresponding to Formula 1, as shown in Scheme 1 is defined below.

Scheme 1

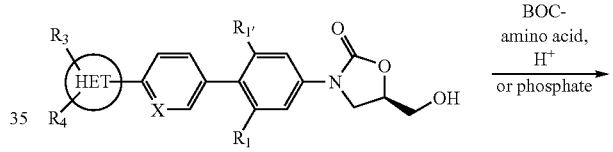

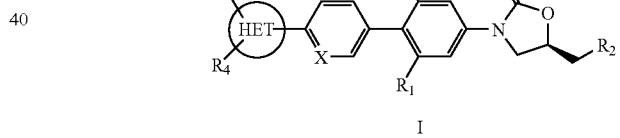

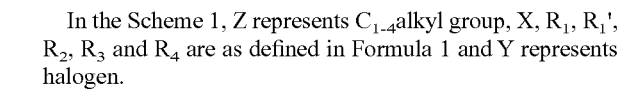

In the Scheme 1, Z represents $C_{1-4}$ alkyl group, X, $R_1$, $R_1'$, $R_2$, $R_3$ and $R_4$ are as defined in Formula 1 and Y represents halogen.

The method of preparing the derivatives of oxazolidinone according to the present invention comprises;

substituting a halogen atom for a hydrogen atom on phenyl of a derivative (II) of hydroxymethyloxazolidinone thereby to form a derivative (III) (Step 1);

substituting stannyl for a halogen atom (Y) of the derivative (III) to form a derivative (IV) (Step 2);

reacting the derivative (IV) with pyridine or phenyl derivative that is substituted to bromine or iodine to form a derivative (V) of oxazolidinone having pyridine ring or phenyl ring (Step 3); and reacting the derivative (V) with amino acid having a protecting group and then with acid thereby to eliminate the protecting group and to form salts of the compounds corresponding to Formula 1, or subjecting the derivative (V) to react with phosphate and then with metallic salt thereby to form salts of the compounds corresponding to Formula 1 (Step 4).

In the Step 1, the derivative (II) of hydroxymethyloxazolidinone may be synthesized by conventional methods. For example, a method may comprise substituting an amino group of anilin for a benzyloxycarbonyl group and reacting a substituted compound with glycidylbutylate in a state of strong bases thereby to form the derivative (II). The state may be prepared by adding a strong base; preferably the strong base may include n-butyllitium, sec-butyllitium, tert-butyllitium, etc., more preferably n-butyllitium. Further, it is preferable to subject the method at a temperature of about −78° C. in liquid nitrogen.

The Step 1 is subjected to substitute a hydrogen atom of phenyl group of the derivative (II) for a halogen atom, preferably for an iodine atom. When the hydrogen atom is substituted for the iodine atom, the substituted reaction may be subjected preferably by adding iodine monochloride (ICl) or trifluoroacetic acid silver salt ($CF_3COOAg$) and adding iodine at room temperature.

The Step 2 is subjected the derivative (III) to react with hexamethylditin, hexabutylditin or tributyltin hydride by adding a catalyst of palladium to form the derivative (IV) of which iodine atom is substituted for a trimethylstannyl group or a tributylstannyl group. The catalyst of palladium may comprise dichlorobistriphenylphosphine palladium (II), tetrakistriphenylphosphine palladium (0), etc. It is preferred to carry out the Step 2 in a solvent of 1,4-dioxan, dimethylformamide, tetrahydrofuran, 1-methyl-2-pyrolidone, etc. at a temperature of about 90 to 150° C.

The Step 3 is carried out by reacting the derivative (IV) with a compound having hetero ring on phenyl or pyridine ring thereby to form the derivative (V). A catalyst of palladium added in the Step 3 may be identical to that of palladium in Step 2. It is preferred to carry out the Step 3 in a solvent of dimethylformamide, 1-methyl-2-pyrolidone, etc. at a temperature of about 100 to 120° C.

The Step 4 is performed by reacting the derivative (V) with amino acid that is protecting an amino group with t-butyloxycarbonyl, dicyclohexylcarbodiimide and 4-dimethylaminopyridine thereby to form the derivative (I) having amino group. The amino acid may include alanine, glycine, proline, isoleucine, leucine, phenylalanine, β-alanine, valine, etc. A solvent comprises dimethylformamide, 1-methyl-2-pyrolidone, etc. Preferably, a reaction by adding the derivative (V) with amino acid is carried out by stirring for about 5 hours above at room temperature.

A mixture of the derivative (V) and amino acid reacts to a strong acid such as trifluoroacetic acid, etc. to eliminate a protecting group. The solvent is removed from the mixture and the mixture is crystallized thereby to provide a salt of the derivative of oxazolidinone corresponding to Formula 1. Preferably, a reaction by adding the derivative (V) with amino acid is carried out by stirring for about 2 hours above at room temperature.

The salt of the derivative of formula 1, prepared by using amino acid at position $R_3$ or $R_4$, in a method known similarly to the above method, may be gained. (S)-3-(4-trimethylstannyl-3-fluorophenyl)-2-oxo-5-oxazolidinylmethyl acetamide as a starting material in the method is known and the method is described in WO0194342.

Further, a phosphate metallic salt of the derivative (I) may be formed by adding sodiummethoxide, sodium hydroxide, etc. to a composition in a solvent such as methanol, ethanol etc., the composition is prepared by dissolving the derivative (V) in trimethylphosphate or triethylphosphate, adding phosphorous oxy chloride and stirring for about 12 hours, at room temperature. The phosphate metallic salt may be produced by reacting the derivative (V) with tetrazole and derivates of amidite at room temperature, oxidizing a reacted compound, synthesizing a derivative of alkylphosphate, eliminating alkyl group using a strong acid thereby to form a derivative of phosphate acid, and converting the derivative of phosphate acid into the phosphate metallic salt by the above-mentioned method.

Further, the present invention provides a pharmaceutical composition comprising the derivatives of oxazolidinone corresponding to Formula 1 for use in an antibiotic.

The oxazolidinone derivatives of the present invention show inhibitory activity against a broad spectrum of bacteria, against methicillin resistant *Staphylococcus aureus* (MRSA) and vancomycin resistant Enterococci (VRE) and have excellent relatively antibiotic activity with a relatively low concentration thereof or in vivo.

Further, the derivatives of the present invention may exert potent antibacterial activity versus various human and animal pathogens, including Gram-positive bacteria such as Staphylococci, Enterococci and Streptococci, anaerobic microorganisms such as *Bacteroides* and Clostridia, and acid-resistant microorganisms such as *Mycobacterium tuberculosis* and *Mycobacterium avium*.

The derivatives of oxazolidinone, having hydroxyl, are reacted with amino acid or phosphate to form prodrugs thereof. The prodrugs have superior solubility to compounds that are not formed as prodrugs: the solubility of the prodrugs represents above 28 mg/ml and the solubility of the compound 10 μg/ml (compound 10). The prodrugs stabilize in water or acidic solution and change to hydroxylmethyl compounds by being reverted using esterase and phosphatase in a blood thereby to develop easy formulation for injection or oral administration.

The composition of the present invention may comprise at least one effective ingredient having functions similar to those of the derivatives of oxazolidinone.

For formulating a pharmaceutical composition, at least one specie of the compound of formula 1 may be admixed with at least one pharmaceutically acceptable carrier. The pharmaceutical acceptable carrier may include saline solution, sterile water, Ringer's solution, buffered saline solution, dextrose solution, malto-dextrin solution, glycerol, ethanol, etc. According to the user's necessity, the pharmaceutical composition may contain conventional expedient such as antioxidizing agent, buffer, soil cleaner, etc. Also, the compositions are admixed with diluents, disintegrants, surface active agents, binders, lubricants, aqueous solution, suspension, etc. to be formed for injection, powders, capsules, granules, tablet, etc. Preferably, the formulation is prepared using proper methods described in Remington's Pharmaceutical Science (the newest edition), Mack Publishing Company, Easton Pa., etc. according to diseases or ingredients.

The compound of the present invention may be administrated orally or parenterally, such as intravenously, hypodermically, intra-abdominally, topically, etc. The dosage of the compound may vary depending upon the particular compound utilized, the mode of administration, the condition, and severity thereof, of the condition being treated, as well as the various physical factors related to the individual being treated. As used in accordance with invention, satisfactory results may be obtained when the compounds of the present invention are administered to the individual in need at a daily dosage of about 10 mg to about 25 mg per kilogram of body weight, preferably about 13 mg to about 20 mg per kilogram of body weight, more preferably administered each of divided doses to many times per day.

The Lethal Dose ($LD_{50}$) of the oxazolidinone derivatives shows above 1 g/kg in test of acute toxicity so that the derivatives are found stable.

(A) Advantageous Effects

The oxazolidinone derivatives of the present invention show inhibitory activity against a broad spectrum of bacteria and lower toxicity. The prodrugs, prepared by reacting the compound having hydroxyl with amino acid or phosphate, have high solubility thereof against water.

Further, the derivatives of the present invention may exert potent antibacterial activity versus various human and animal pathogens, including Gram-positive bacteria such as Staphylococci, Enterococci and Streptococci, anaerobic microorganisms such as *Bacteroides* and Clostridia, and acid-resistant microorganisms such as *Mycobacterium tuberculosis* and *Mycobacterium avium*.

Accordingly, the compositions comprising the derivatives of oxazolidinone are used in an antibiotic.

DETAILED DESCRIPTION OF THE PREFERRED EMBODIMENT

(b) Best Mode for Carrying Out the Invention

The examples are given solely for the purpose of illustration and are not to be construed as limitations of the present invention, as many variations thereof are possible without departing from the spirit and scope of the invention.

Preparation Example 1

Preparation of N-Carbobenzyloxy-3-fluoroaniline 3-fluoroaniline 100 g was dissolved in 1 L of tetrahydrofuran (THF) and the solution was added with 150 g (1.8 mol) of sodium bicarbonate ($NaHCO_3$). After being cooled to 0° C., the solution was slowly added with 154 ml of N-carbobenzyloxy chloride (CbzCl) for reaction. While the temperature was maintained at 0° C., the reaction mixture was let to react for 2 hours with stirring. Afterwards, the reaction was extracted with 0.5 L of ethyl acetate. The organic layer, after being separated, was washed with brine, dried over anhydrous magnesium sulfate ($MgSO_4$) and concentrated in vacuo. The residue was washed twice with n-hexane to afford the title compound as white crystal. 132 g. Yield 85%.

Preparation Example 2

Preparation of (R)-3-(3-fluorophenyl)-2-oxo-5-oxazolidinylmethanol 123 g of N-carbobenzyloxy-3-fluoroaniline 132 g prepared in the Preparation example 1 was dissolved in 1.3 L of tetrahydrofuran and the solution was cooled to −78° C. 370 ml of n-butyllithium (n-BuLi, 1.6M/n-hexane) was slowly added to the solution in a nitrogen atmosphere, followed by stirring for 10 min. And 84 ml of (R)-(−)-glycidylbutylate was slowly added to the reaction mixture, stirred at the same temperature for 2 hours and allowed to react for 24 hours at room temperature. After completion of the reaction, the solution was added with ammonium chloride ($NH_4Cl$) solution and extracted with 0.5 L of ethyl acetate at room temperature. The organic layer, thus separated, was washed with brine, dried over anhydrous magnesium sulfate and concentrated in vacuo. The residue was dissolved in 100 ml of ethyl acetate and washed with n-hexane to give white crystals, which were purified to the title compound. 80 g. Yield 70%.

$^1$H NMR (DMSO-$d_6$) δ 7.85 (t, 1H), 7.58 (dd, 1H), 7.23 (dd, 1H), 4.69 (m, 1H), 4.02 (t, 1H), 3.80 (dd, 1H), 3.60 (br dd, 2H).

Preparation Example 3

Preparation of (R)-3-(4-iodo-3-fluorophenyl)-2-oxo-5-oxazolidinylmethanol

In 300 ml of acetonitrile was dissolved 30 g of (R)-3-(3-fluorophenyl)-2-oxo-5-oxazolidinylmethanol prepared in the Preparation example 2, and 46 g of trifluoroacetic acid silver salt ($CF_3COOAg$) and 43 g of iodide were added to the solution. After being stirred for one day at room temperature, the solution was added with water and was extracted with ethyl acetate. The organic layer, thus separated, was washed with brine and dehydrated. And then the residue was filtered, concentrated in vacuo and dried thereby to form the title compound 44 g. Yield 94%.

$^1$H NMR (DMSO-$d_6$) δ 7.77 (t, 1H), 7.56 (dd, 1H), 7.20 (dd, 1H), 5.20 (m, 1H), 4.70 (m, 1H), 4.07 (t, 1H), 3.80 (m, 1H), 3.67 (m, 2H), 3.56 (m, 3H)

Preparation Example 4

Preparation of (R)-3-(4-trimethylstannyl-3-fluorophenyl)-2-oxo-5-oxazolidinylmethanol In 660 ml of 1,4-dioxane was dissolved 50 g of (R)-3-(4-iodo-3-fluorophenyl)-2-oxo-5-oxazolidinylmethanol prepared in the Preparation example 3, 52 g of hexabutylditin (($Bu_3Sn)_2$) and 9.3 g of dichlorobistriphenylphosphine palladium were added into the solution, and stirred for 2 hours. The solution was filtered using celite and concentrated in vacuo. The residue was purified by column chromatography and 45 g of the title compound was formed.

$^1$H NMR (DMSO-$d_6$) δ 7.74 (m, 3H), 5.20 (t, 1H), 4.71 (m, 1H), 4.08 (t, 1H), 3.82 (dd, 1H), 3.68 (m, 1H), 3.52 (m, 1H), 1.48 (m, 6H), 1.24 (m, 6H), 1.06 (m, 6H), 0.83 (t, 9H)

Preparation Example 5

Preparation of 2-cyano-5-bromopyridine

In 1 L of dimethylformamide was dissolved 100 g of 2,5-dibromopyridine, 32 g of cupper cyanide and 17.8 g of sodium cyanide were added to the solution at room temperature and the solution was stirred at the temperature of 150° C. for 7 hours for reaction. After being cooled to room temperature, the reaction mixture was added with water and extracted with ethyl acetate. The organic layer was washed with brine, dehydrated, filtered and concentrated in vacuo. The title compound 54 g was obtained. Yield 70%.

$^1$H NMR ($CDCl_3$) δ 8.76 (s, 1H), 7.98 (dd, 1H), 7.58 (dd, 1H)

Preparation Example 6

Preparation of 2-(tetrazol-5-yl)-5-bromopyridine 10 g of 2-cyano-5-bromopyridine prepared in the Preparation example 5 was dissolved in 100 ml of dimethylformamide, 5.33 g of sodiumazide, and 4.4 g of ammoniumchloride were added to the solution at room temperature, and the solution was stirred at the temperature of 110° C. for 3 hours for reaction. The reaction mixture was added with water and then was extracted with ethyl acetate. The organic layer, thus separated, was washed with brine, dehydrated, filtrated and concentrated in vacuo thereby to obtain 10.5 g of the title compound. Yield 85%.

Preparation Example 7

Preparation of 2-(1-methyltetrazol-5-yl)-5-bromopyridine and 2-(2-methyltetrazol-5-yl)-5-bromopyridine 10.5 g of 2-(tetrazol-5-yl)-5-bromopyridine prepared in the Preparation example 6 was dissolved in 100 ml of dimethylformamide. And then 6.5 g of sodiumhydroxide was added to the solution and 9.3 g of iodomethane was slowly added to the solution at the temperature of 0° C. The solution was stirred for 6 hours at room temperature, added with water, extracted with ethyl acetate. And then the organic layer was washed with brine, dehydrated, filtrated, concentrated in vacuo and purified by column chromatography to obtain 4 g of 2-(1-methyltetrazol-5-yl)-5-bromopyridine and 5 g of 2-(2-methyltetrazol-5-yl)-5-bromopyridine.

1) 2-(1-methyltetrazol-5-yl)-5-bromopyridine $^1$H NMR (CDCl$_3$) δ 8.77 (t, 1H), 8.23 (dd, 1H), 8.04 (dd, 1H), 4.46 (s, 3H)

2) 2-(2-methyltetrazol-5-yl)-5-bromopyridine $^1$H NMR (CDCl$_3$) δ 8.80 (t, 1H), 8.13 (dd, 1H), 7.98 (dd, 1H), 4.42 (s, 3H)

Preparation Example 8

Preparation of 2-(2-methyl-[1,3,4]oxadiazol-5-yl)-5-bromopyridine

In 130 ml of acetic anhydride was dissolved 8.6 g of 2-(tetrazol-5-yl)-5-bromopyridine prepared in the Preparation example 6. And then the solution was added with 15 ml of pyridine and stirred for 3 hours for reaction. The reaction mixture was added with ethyl acetate and extracted to separate organic layer. And then the organic layer was washed with water and brine. The organic layer was dehydrated, filtrated and concentrated in vacuo to give 7.3 g of the title compound. Yield 80%.

$^1$H NMR (CDCl$_3$) δ 7.99 (t, 1H), 7.40 (dd, 1H), 7.27 (dd, 1H), 1.83 (s, 3H)

Preparation Example 9

Preparation of 2-([1,2,3]triazol-1-yl)-5-bromopyridine and 2-([1,2,3]triazol-2-yl)-5-bromopyridine 20 g of 2,5-dibromopyridine was dissolved in 200 ml of 1-methyl-2-pyrrolidone. The solution was added with 35 g of potassium carbonate and stirred for 10 hours at the temperature of 100° C. The reaction mixture was added with ethyl acetate and the organic layer, thus obtained was washed with water and brine. The organic layer was dried, filtered and concentrated in vacuo to provide 6 g of 2-([1,2,3]triazol-1-yl)-5-bromopyridine, 4 g of 2-([1,2,3]triazol-2-yl)-5-bromopyridine.

1) 2-([1,2,3]triazol-1-yl)-5-bromopyridine $^1$H NMR (CDCl$_3$) δ 8.53 (dd, 2H), 8.10 (d, 1H), 8.03 (dd, 1H), 7.82 (s, 1H)

2) 2-([1,2,3]triazol-2-yl)-5-bromopyridine $^1$H NMR (CDCl$_3$) δ 8.60 (t, 1H), 7.97 (s, 2H), 7.87 (s, 2H)

Example 1

Preparation of (R)-3-(4-(2-(2-methyltetrazol-5-yl)pyridin-5-yl)-3-fluorophenyl)-5-hydroxymethyl oxazolidin-2-one (compound 10)

In 150 ml of 1-methyl-2-pyrrolidone was dissolved 37 g of (R)-3-(4-tributhylstannyl-3-fluorophenyl)-2-oxo-5-oxazolidinylmethanol. The solution was added with 19.7 g of 2-(2-methyltetrazol-5-yl)-5-bromopyridine, 10.44 g of lithium chloride and 2.9 g of dichlorobistriphenylphosphine palladium (II) at room temperature and then stirred at the temperature of 120° C. for 4 hours. The reaction mixture was added with water and then extracted with ethyl acetate. The organic layer, thus separated, was washed with brine, dehydrated, filtrated, concentrated in vacuo and purified by column chromatography to provide 8 g of the title compound. Yield 26%.

$^1$H NMR (DMSO-d$_6$) δ 8.90 (s, 1H), 8.18 (m, 2H), 7.70 (m, 2H), 7.49 (dd, 1H), 5.25 (t, 1H), 4.74 (m, 1H), 4.46 (s, 3H), 4.14 (t, 1H), 3.88 (dd, 1H), 3.68 (m, 1H), 3.58 (m, 1H)

Example 2

Preparation of (R)-3-(4-(2-(2-methyl-[1,3,4]oxadiazol-5-yl)pyridin-5-yl)-3-fluorophenyl)-5-hydroxymethyl oxazolidin-2-one (compound 16)

The title compound 6.6 g (yield 30%) was prepared in a method similar to that of Example 1, except that, 14.3 g of 2-(2-methyl-[1,3,4]oxadiazol-5-yl)-5-bromopyridine, instead of 2-(2-methyltetrazol-5-yl)-5-bromopyridine, was used as a starting material.

$^1$H NMR (DMSO-d$_6$) δ 8.93 (s, 1H), 8.21 (s, 2H), 7.71 (m, 2H), 7.50 (dd, 1H), 5.25 (t, 1H), 4.74 (m, 1H), 4.14 (t, 1H), 3.89 (dd, 1H), 3.68 (m, 1H), 3.59 (m, 1H), 2.64 (s, 3H)

Example 3

Preparation of (R)-3-(4-(2-([1,2,4]triazol-1-yl)pyridin-5-yl)-3-fluorophenyl)-5-hydroxymethyl oxazolidin-2-one (compound 17)

The same procedure as in Example 1 was conducted, except for using, instead of 2-(2-methyltetrazol-5-yl)-5-bromopyridine, 200 mg of 2-([1,2,4]triazol-1-yl)-5-bromopyridine as a starting material, to prepare the title compound 150 mg (yield 48%).

Example 4

Preparation of (R)-3-(4-(4-(4,5-dimethyloxzol-2-yl)phenyl)-3-fluorophenyl)-5-hydroxymethyl oxazolidin-2-one (compound 21)

The same procedure as in Example 1 was conducted, except for using, instead of 2-(2-methyltetrazol-5-yl)-5-bromopyridine, 1 g of 4-(4,5-dimethyloxazol-2-yl)bromobenzene as a starting material, to prepare the title compound 780 mg (yield 76%).

$^1$H NMR (DMSO-d$_6$) δ 7.96 (s, 1H), 7.94 (s, 1H), 7.63 (m, 4H), 7.44 (dd, 1H), 5.23 (t, 1H), 4.72 (m, 1H), 4.12 (t, 1H), 3.87 (dd, 1H), 3.68 (m, 1H), 3.56 (m, 1H), 2.32 (s, 3H), 2.10 (s, 3H)

Example 5

Preparation of (R)-3-(4-(2-([1,2,3]triazol-1-yl)pyridin-5-yl)-3-fluorophenyl)-5-hydroxymethyloxazolidin-2-one (compound 24)

The same procedure as in Example 1 was conducted, except for using, instead of 2 (2-methyltetrazol-5-yl)-5-bromopyridine, 2 g of 2-([1,2,3]triazol-1-yl)-5-bromopyridine as a starting material, to prepare the title compound 1.2 g.

$^1$H NMR (DMSO-d$_6$) δ 8.88 (s, 1H), 8.76 (s, 1H), 8.28 (d, 1H), 8.21 (d, 1H), 8.01 (s, 1H), 7.70 (m, 2H), 7.51 (dd, 1H), 5.26 (t, 1H), 4.75 (m, 1H), 4.14 (t, 1H), 3.90 (dd, 1H), 3.68 (m, 1H), 3.58 (m, 1H)

Example 6

Preparation of (R)-3-(4-(2-([1,2,3]triazol-2-yl)pyridin-5-yl)-3-fluorophenyl)-5-hydroxymethyl oxazolidin-2-one (compound 29)

The same procedure as in Example 1 was conducted, except for using, instead of 2-(2-methyltetrazol-5-yl)-5-bromopyridine, 1 g of 2-([1,2,3]triazol-2-yl)-5-bromopyridine as a starting material, to prepare the title compound 0.7 g.

$^1$H NMR (DMSO-d$_6$) δ 8.74 (s, 1H), 8.25 (dd, 1H), 8.23 (s, 1H), 8.11 (d, 1H), 7.69 (m, 3H), 7.49 (dd, 1H), 5.24 (t, 1H), 4.75 (m, 1H), 4.14 (t, 1H), 3.89 (dd, 1H), 3.68 (m, 1H), 3.59 (m, 1H)

Example 7

Preparation of (R)-3-(4-(4-(4-cyanomethyl thiazol-2-yl)phenyl)-3-fluorophenyl)-5-hydroxymethyl oxazolidin-2-one (compound 32)

The same procedure as in Example 1 was conducted, except for using, instead of 2-(2-methyltetrazol-5-yl)-5-bromopyridine, 1 g of 4-(4-cyanomethyl thiazol-2-yl)bromobenzene as a starting material, to prepare the title compound 520 mg.

$^1$H NMR (DMSO-d$_6$) δ 8.04 (s, 1H), 8.00 (s, 1H), 7.65 (m, 5H), 7.47 (dd, 1H), 5.24 (t, 1H), 4.74 (m, 1H), 4.23 (s, 2H), 4.13 (t, 1H), 3.88 (dd, 1H), 3.68 (m, 1H), 3.59 (m, 1H)

Example 8

Preparation of (R)-3-(4-(2-(2-methyltetrazol-5-yl) pyridin-5-yl)-3,5-difluorophenyl)-5-hydroxymethyl oxazolidin-2-one (compound 38)

The same procedure as in Example 1 was conducted, except for using, instead of (R)-3-(4-trimethylstannyl-3-fluorophenyl)-2-oxo-5-oxazolidinylmethanol, (R)-3-(4-trimethylstannyl-3,4-difluorophenyl)-2-oxo-5-oxazolidinylmethanol as a starting material, to prepare the title compound.

$^1$H NMR (DMSO-d$_6$) δ 8.81 (s, 1H), 8.25 (d, 1H), 8.10 (d, 1H), 7.54 (d, 2H), 5.25 (t, 1H), 4.77 (m, 1H), 4.47 (s, 3H), 4.13 (t, 1H), 3.89 (dd, 1H), 3.68 (m, 1H), 3.57 (m, 1H)

Example 9

Preparation of (R)-3-(4-(2-(2-methyl-[1,3,4]oxadiazol-5-yl)pyridin-5-yl)-3,4-difluorophenyl)-5-hydroxymethyl oxazolidin-2-one (compound 39)

The same procedure as in Example 1 was conducted by using (R)-3-(4-trimethylstannyl-3,4-difluorophenyl)-2-oxo-5-oxazolidinylmethanol and 2-(2-methyl-[1,3,4]oxadiazol-5-yl)-5-bromopyridine as a starting material, to prepare the title compound.

$^1$H NMR (DMSO-d$_6$) δ 8.83 (s, 1H), 8.25 (d, 1H), 8.15 (d, 1H), 7.55 (d, 2H), 5.25 (t, 1H), 4.77 (m, 1H), 4.13 (t, 1H), 3.89 (dd, 1H), 3.68 (m, 1H), 3.59 (m, 1H), 2.63 (s, 3H)

Example 10

Preparation of (R)-3-(4-(2-(2-methyltetrazol-5-yl) pyridin-5-yl)-3-fluorophenyl)-5-glycyloxymethyl oxazolidin-2-one trifluoroacetic acid (compound 12)

In 25 ml of dimethylformamide was dissolved 4 g of (R)-3-(4-(2-(2-methyltetrazol-5-yl)pyridin-5-yl)-3-fluorophenyl)-5-hydroxymethyl oxazolidin-2-one (compound 10). The solution was added 3.34 g of 1,3-dicyclohexylcarbodiimide, 2.36 g of BOC-glycine and 0.2 g of 4-dimethylaminopyridine at room temperature and then stirred for hours. The reaction mixture was added with water and extracted with ethyl acetate. The organic layer, thus separated, was washed with brine, dehydrated, filtered, concentrated in vacuo and purified by column chromatography. A residue, thus resulted in concentrating in vacuo, was dissolved in 70 ml of methylene chloride, added with 30 ml of trifluoroacetic acid, and stirred for 2 hours at room temperature. The residue was washed with ethanol and ethyl ether and concentrated in vacuo to obtain the title compound 4.47 g. Yield 76%.

$^1$H NMR (DMSO-d$_6$) δ 8.92 (s, 1H), 8.19 (s, 3H), 8.17 (m, 2H), 7.77 (t, 1H), 7.69 (dd, 1H), 7.49 (dd, 1H), 5.00 (m, 1H), 4.46 (m, 2H), 4.47 (s, 3H), 4.24 (t, 1H), 3.92 (dd, 1H), 3.90 (s, 2H)

Example 11

Preparation of (R)-3-(4-(2-(2-methyltetrazol-5-yl) pyridin-5-yl)-3-fluorophenyl)-5-(L-valyloxy)methyl oxazolidin-2-one trifluoroacetic acid (compound The title compound was prepared in a method similar to that of Example using BOC-valine, instead of BOC-glycine.

$^1$H NMR (DMSO-d$_6$) δ 8.92 (s, 1H), 8.40 (s, 3H), 8.21 (m, 2H), 7.76 (t, 1H), 7.65 (dd, 1H), 7.48 (dd, 1H), 5.05 (m, 1H), 4.63 (dd, 1H), 4.47 (s, 3H), 4.43 (dd, 1H), 4.28 (t, 1H), 4.01 (d, 1H), 3.93 (dd, 1H), 2.14 (m, 1H), 0.98 (d, 3H), 0.95 (d, 3H)

Example 12

Preparation of (R)-3-(4-(2-[1,2,3]triazol-1-yl pyridin-5-yl)-3-fluorophenyl)-5-glycyloxymethyl oxazolidin-2-one trifluoroacetic acid (compound 22)

The title compound was prepared in a method similar to that of Example using compound 24.

$^1$H NMR (DMSO-d$_6$) δ 8.87 (s, 1H), 8.76 (s, 1H), 8.33 (s, 3H), 8.29 (d, 1H), 8.00 (s, 1H), 7.77 (t, 1H), 7.76 (t, 1H), 7.67 (dd, 1H), 7.47 (dd, 1H), 5.02 (m, 1H), 4.49 (m, 2H), 4.23 (t, 1H), 3.93 (m, 3H)

Example 13

Preparation of (R)-3-(4-(4-(4,5-dimethyloxazol-2-yl) phenyl)-3-fluorophenyl)-5-glycyloxymethyl oxazolidin-2-one trifluoroacetic acid (compound 23)

The title compound was prepared in a method similar to that of Example using compound 21.

$^1$H NMR (DMSO-d$_6$) δ 8.31 (s, 3H), 7.97 (d, 2H), 7.64 (m, 4H), 7.45 (dd, 1H), 5.01 (m, 1H), 4.47 (m, 2H), 4.25 (t, 1H), 3.94 (dd, 1H), 3.90 (s, 2H)

Example 14

Preparation of (R)-3-(4-(2-(2-methyl-[1,3,4]oxadiazol-5-yl)pyridin-5-yl)-3-fluorophenyl)-5-glycyloxymethyl oxazolidin-2-one trifluoroacetic acid (compound 27)

The title compound was prepared in a method similar to that of Example using compound 16.

$^1$H NMR (DMSO-d$_6$) δ 8.96 (s, 1H), 8.31 (s, 3H), 8.22 (s, 2H), 7.76 (t, 1H), 7.66 (dd, 1H), 7.50 (dd, 1H), 5.04 (m, 1H), 4.50 (m, 2H), 4.25 (t, 1H), 3.94 (dd, 1H), 3.91 (s, 2H), 2.63 (s, 3H)

Example 15

Preparation of (R)-3-(4-(4-(4-cyanomethyl thiazol-2-yl)phenyl)-3-fluorophenyl)-5-glycyloxymethyl oxazolidin-2-one trifluoroacetic acid (compound The title compound was prepared in a method similar to that of Example using compound 32.

$^1$H NMR (DMSO-d$_6$) δ 8.25 (s, 3H), 8.03 (d, 2H), 7.68 (m, 5H), 7.44 (dd, 1H), 5.01 (m, 1H), 4.48 (m, 2H), 4.25 (m, 3H), 3.92 (m, 3H)

Example 16

Preparation of (R)-3-(4-(2-([1,2,3]triazol-2-yl)pyridin-5-yl)-3-fluorophenyl)-5-glycyloxymethyl oxazolidin-2-one trifluoroacetic acid (compound The title compound was prepared in a method similar to that of Example using compound 29.

$^1$H NMR (DMSO-d$_6$) δ 8.78 (s, 1H), 8.23 (m, 2H), 8.22 (s, 3H), 8.20 (s, 1H), 8.12 (d, 1H), 7.75 (t, 1H), 7.67 (dd, 1H), 7.48 (dd, 1H), 5.01 (m, 1H), 4.49 (m, 2H), 4.24 (t, 1H), 3.92 (dd, 1H), 3.89 (s, 2H)

Example 17

Preparation of (S)-3-(4-(2-(2-oxo-4-glycyloxymethylpyrrolidin-1-yl)pyridin-5-yl)-3-fluorophenyl)-2-oxo-5-oxazolidinylmethyl acetamide trifluoroacetic acid (compound 1)

1. The Primary Step

In 14 ml of 1-methyl-2-pyrrolidone was dissolved 1.8 g of (S)-3-(4-trimethylstannyl-3-fluorophenyl)-2-oxo-5-oxazolidinylmethyl acetamide. The solution was added 1.03 g of 2-(2-oxo-4-hydroxymethylpyrrolidin-1-yl)-5-bromopyridine, 0.55 g of lithium chloride and 0.15 g of dichlorobis-triphenylphosphine palladium (II) at room temperature and then stirred at the temperature of 110° C. for 2 hours. The reaction mixture was added with water and extracted with ethyl acetate. After being washed with brine, the organic layer, thus separated, was dehydrated, filtered, concentrated in vacuo and purified by column chromatography thereby to obtain (S)-3-(4-(2-(2-oxo-4-hydroxymethylpyrrolidin-1-yl) pyridin-5-yl)-3-fluorophenyl)-2-oxo-5-oxazolidinylmethyl acetamide 410 mg. Yield 21%.

2. The Secondary Step

In dimethylformamide 2.3 ml was dissolved 50 mg of the compound prepared in the primary step. The solution was added with 35 mg of 1,3-dicyclohexylcarbodiamide, 25 mg of BOC-glycine and 2.1 mg of 4-dimethylaminopyridine at room temperature and then stirred for 10 hours. The reaction mixture was added with water and extracted with ethyl acetate. After being washed with brine, the organic layer, thus separated, was dehydrated, filtrated, concentrated in vacuo and purified by column chromatography. A residue, provided by concentrating, was dissolved in 2 ml of methylene chloride, added with 1 ml of trifluoroacetic acid and then stirred for 2 hours at room temperature. The residue was washed with ethanol and ethyl ether, evaporated in vacuo to obtain the title compound 140 mg.

$^1$H NMR (DMSO-d$_6$) δ 8.60 (s, 1H), 8.40 (d, 1H), 8.28 (s, 3H), 8.25 (m, 1H), 8.08 (dd, 1H), 7.63 (m, 2H), 7.42 (dd, 1H), 4.76 (m, 1H), 4.27 (s, 2H), 4.16 (q, 2H), 3.87 (s, 2H), 3.80 (m, 2H), 3.42 (m, 2H), 2.62 (m, 1H), 2.11 (m, 1H), 1.83 (s, 3H)

Example 18

Preparation of (S)-3-(4-(2-(4-glycyloxymethyl-[1,2,3]triazol-1-yl)pyridin-5-yl)-3-fluorophenyl)-2-oxo-5-oxazolidinylmethyl acetamide trifluoroacetic acid (compound 2)

The same procedure as in Example 17 was conducted, except for using, instead of 2-(2-oxo-4-hydroxymethylpyrrolidin-1-yl)-5-bromopyridine, 2-(4-hydroxymethyl-[1,2,3] triazol-1-yl)-5-bromopyridine as a starting material, to prepare the title compound.

$^1$H NMR (DMSO-d$_6$) δ 8.96 (s, 1H), 8.89 (s, 1H), 8.22 (m, 6H), 7.74 (t, 1H), 7.68 (dd, 1H), 7.48 (dd, 1H), 5.42 (s, 2H), 4.78 (m, 1H), 4.19 (t, 1H), 3.91 (s, 2H), 3.79 (dd, 1H), 3.43 (m, 2H), 1.83 (s, 3H)

Example 19

Preparation of (S)-3-(4-(2-(5-glycyloxymethylisoxazol-3-yl)pyridin-5-yl)-3-fluorophenyl)-2-oxo-5-oxazolidinylmethyl acetamide trifluoroacetic acid (compound 3)

The same procedure as in Example 17 was conducted, except for using, instead of 2-(2-oxo-4-hydroxymethylpyrrolidin-1-yl)-5-bromopyridine, 2-(5-hydroxymethylisoxazol)-5-bromopyridine as a starting material, to prepare the title compound.

$^1$H NMR (DMSO-d$_6$) δ 8.89 (s, 1H), 8.26 (s, 3H), 8.12 (m, 2H), 7.72 (t, 1H), 7.64 (dd, 1H), 7.48 (dd, 1H), 7.21 (s, 1H), 5.49 (s, 2H), 4.77 (m, 1H), 4.17 (t, 1H), 3.98 (s, 2H), 3.79 (m, 1H), 3.43 (m, 2H), 1.83 (s, 3H)

Example 20

Preparation of (S)-3-(4-(2-(2-oxo-3-glycyloxypyrrolidin-1-yl)pyridin-5-yl)-3-fluorophenyl)-2-oxo-5-oxazolidinylmethyl acetamide trifluoroacetic acid (compound 5)

The same procedure as in Example 17 was conducted, except for using, instead of 2-(2-oxo-4-hydroxymethylpyrrolidin-1-yl)-5-bromopyridine, 2-(2-oxo-3-hydroxypyrrolidin-1-yl)-5-bromopyridine as a starting material, to prepare the title compound.

$^1$H NMR (DMSO-$d_6$) δ 8.60 (s, 1H), 8.33 (d, 1H), 8.28 (s, 3H), 8.25 (m, 1H), 8.05 (d, 1H), 7.63 (m, 2H), 7.42 (dd, 1H), 5.78 (t, 1H), 4.78 (m, 1H), 4.16 (q, 2H), 3.98 (s, 2H), 3.85 (m, 1H), 3.78 (m, 1H), 3.43 (m, 2H), 2.62 (m, 1H), 2.12 (m, 1H), 1.83 (s, 3H)

Example 21

Preparation of (S)-3-(4-(2-(5-glycyloxymethyl-[1,2,4]oxadiazol-3-yl)pyridin-5-yl)-3-fluorophenyl)-2-oxo-5-oxazolidinylmethyl acetamide trifluoroacetic acid (compound 6)

The same procedure as in Example 17 was conducted, except for using, instead of 2-(2-oxo-4-hydroxymethylpyrrolidin-1-yl)-5-bromopyridine, 2-(5-hydroxymethyl-[1,2,4]oxadiazol-3-yl)-5-bromopyridine as a starting material, to prepare the title compound.

$^1$H NMR (DMSO-$d_6$) δ 8.95 (s, 1H), 8.32 (s, 3H), 8.21 (m, 3H), 7.75 (t, 1H), 7.65 (dd, 1H), 7.47 (d, 1H) 5.67 (s, 1H), 4.78 (m, 1H), 4.18 (t, 1H), 4.05 (s, 2H), 3.80 (m, 1H), 3.43 (m, 2H), 1.83 (s, 3H)

Example 22

Preparation of (S)-3-(4-(2-(5-glycyloxymethyl-4,5-dihydroisoxazol-3-yl)pyridin-5-yl)-3-fluorophenyl)-2-oxo-5-oxazolidinylmethyl acetamide trifluoroacetic acid (compound 7)

The same procedure as in Example 17 was conducted, except for using, instead of 2-(2-oxo-4-hydroxymethylpyrrolidin-1-yl)-5-bromopyridine, 2-(5-hydroxymethyl-4,5-dihydroisoxazol-1-yl)-5-bromopyridine as a starting material, to prepare the title compound.

$^1$H NMR (DMSO-$d_6$) δ 8.81 (s, 1H), 8.27 (t, 1H), 8.24 (s, 3H), 8.05 (m, 2H), 7.69 (m, 2H), 7.44 (d, 1H) 5.04 (m, 1H), 4.76 (m, 1H), 4.41 (dd, 1H), 4.32 (m, 1H), 4.17 (t, 1H), 3.86 (s, 2H), 3.77 (m, 1H), 3.60 (m, 1H), 3.44 (m, 2H), 1.83 (s, 3H)

Example 23

Preparation of (S)-3-(4-(4-(4-glycyloxymethylthiazol-2-yl)phenyl)-3-fluorophenyl)-2-oxo-5-oxazolidinylmethyl acetamide trifluoroacetic acid (compound 30)

The same procedure as in Example 17 was conducted, except for using, instead of 2-(2-oxo-4-hydroxymethylpyrrolidin-1-yl)-5-bromopyridine, 4-(4-hydroxymethyl thiazol-2-yl)-bromobenzene as a starting material, to prepare the title compound.

$^1$H NMR (DMSO-$d_6$) δ 8.25 (s, 3H), 8.00 (d, 2H), 7.85 (s, 1H), 7.69 (m, 4H), 7.44 (dd, 1H), 5.63 (s, 2H), 4.76 (m, 1H), 4.16 (t, 1H), 3.93 (s, 2H), 3.79 (dd, 1H), 3.43 (m, 2H), 1.83 (s, 3H)

Example 24

Preparation of (R)-3-(4-(2-(2-methyltetrazol-5-yl)pyridin-5-yl)-3-fluorophenyl)-5-([1,2,4]triazol-1-yl)methyl oxazolidin-2-one (compound 4)

1. The Primary Step

In 14 ml of methylene chloride was dissolved 1 g of (R)-3-(4-(2-(2-methyltetrazol-5-yl)pyridin-5-yl)-3-fluorophenyl)-5-hydroxymethyl oxazolidin-2-one (compound 10). The solution was added with 0.46 g of methanesulfonylchloride 0.46 g and 0.75 ml of triethylamine at room temperature and stirred at the same temperature for 30 minutes. Water and brine were added to the reaction mixture for washing, followed by extraction. The organic layer was dehydrated, filtrated and concentrated in vacuo thereby to provide (R)-3-(4-(2-(2-methyltetrazol-5-yl)pyridin-5-yl)-3-fluorophenyl)-5-methanesulfonyloxymethyl oxazolidin-2-one 1 g. Yield 82%.

2. The Secondary Step

In 15 ml of dimethylformamide was dissolved the compound prepared in the primary step. The solution was added with 300 mg of 1,2,4-triazol 300 mg and 100 mg of sodiumhydride (60%) at room temperature and stirred for 2 days. The reaction mixture was extracted with ethyl acetate and then the organic layer, thus separated, was washed with water and brine. The organic layer was dehydrated, filtered and concentrated in vacuo. The residue, prepared by concentrating, was purified by column chromatography to provide the title compound 400 mg. Yield 43%.

$^1$H NMR (DMSO-$d_6$) δ 8.91 (s, 1H), 8.57 (s, 1H), 8.19 (m, 2H), 7.74 (t, 1H), 7.58 (dd, 1H), 7.42 (dd, 1H), 5.13 (m, 1H), 4.64 (m, 2H), 4.46 (s, 3H), 4.28 (t, 1H), 3.99 (dd, 1H)

Example 25

Preparation of (R)-3-(4-(2-(2-methyltetrazol-5-yl)pyridin-5-yl)-3-fluorophenyl)-5-([1,2,3]triazol-2-yl)methyl oxazolidin-2-one (compound 8) and (R)-3-(4-(2-(2-methyltetrazol-5-yl)pyridin-5-yl)-3-fluorophenyl)-5-([1,2,3]triazol-1-yl)methyl oxazolidin-2-one (compound 9)

The same procedure as in Example 24 was conducted, except for adding, instead of 1,2,4-triazol, 1,2,3-triazol, to obtain compound 8 and compound 9, and then the compounds were divided by column chromatography.

(compound 8) $^1$H NMR (DMSO-$d_6$) δ 8.90 (s, 1H), 8.19 (m, 2H), 7.82 (s, 2H), 7.71 (t, 1H), 7.59 (dd, 1H) 7.41 (dd, 1H), 5.22 (m, 1H), 4.86 (m, 2H), 4.46 (s, 3H), 4.30 (t, 1H), 3.98 (dd, 1H)

(compound 9) $^1$H NMR (DMSO-$d_6$) δ 8.90 (s, 1H), 8.18 (m, 3H), 7.75 (s, 1H), 7.72 (t, 1H), 7.59 (dd, 1H) 7.42 (dd, 1H), 5.22 (m, 1H), 4.86 (m, 2H), 4.46 (s, 3H), 4.30 (t, 1H), 3.98 (dd, 1H)

Example 26

Preparation of (R)-3-(4-(2-(2-methyl-[1,3,4]oxadiazol-5-yl)pyridin-5-yl)-3-fluorophenyl)-5-([1,2,3]triazol-1-yl)methyl oxazolidin-2-one (compound 13)

The same procedure as in Example 24 was conducted, except for adding 1,2,3-triazole and using the compound 16 as a starting material, to obtain the title compound.

$^1$H NMR (DMSO-$d_6$) δ 8.92 (s, 1H), 8.20 (s, 2H), 8.17 (s, 1H), 7.75 (s, 1H), 7.73 (t, 1H), 7.61 (dd, 1H) 7.43 (dd, 1H), 5.18 (m, 1H), 4.85 (m, 2H), 4.29 (t, 1H), 3.96 (dd, 1H), 2.62 (s, 3H)

Example 27

Preparation of (R)-3-(4-(2-([1,2,4]triazol-1-yl)pyridin-5-yl)-3-fluorophenyl)-5-([1,2,3]triazol-1-yl)methyl oxazolidin-2-one (compound 14)

The same procedure as in Example 24 was conducted, except for adding 1,2,3-triazole and using the compound 17 as a starting material, to obtain the title compound.

¹H NMR (DMSO-d₆) δ 9.40 (s, 1H), 8.70 (s, 1H), 8.32 (s, 2H), 8.25 (d, 1H), 8.17 (s, 1H), 7.96 (d, 1H), 7.75 (s, 1H), 7.71 (t, 1H), 7.60 (dd, 1H) 7.42 (dd, 1H), 5.18 (m, 1H), 4.86 (m, 2H), 4.29 (t, 1H), 3.96 (dd, 1H)

Example 28

Preparation of (R)-3-(4-(2-(2-methyltetrazol-5-yl) pyridin-5-yl)-3-fluorophenyl)-5-fluoromethyl oxazolidin-2-one (compound 18)

In 5 ml of methylene chloride was dissolved 100 mg of the compound 10. The solution was added with 43 mg of diethylaminosulfurtrifloride (DAST) and 0.078 ml of triethylamine and then stirred for 24 hours. After being concentrating, the reaction mixture was purified by column chromatography to obtain the title compound 75 mg. Yield 75%.

¹H NMR (DMSO-d₆) δ 8.91 (s, 1H), 8.19 (m, 2H), 7.74 (t, 1H), 7.66 (dd, 1H) 7.49 (dd, 1H), 5.06 (m, 1H), 4.89 (m, 2H), 4.46 (s, 3H), 4.23 (t, 1H), 3.95 (dd, 1H)

Example 29

Preparation of (S)-3-(4-(2-(imidazol-1-yl)pyridin-5-yl)-3-fluorophenyl)-5-aminomethyl oxazolidin-2-one hydrochloride (compound 19)

In 3.4 ml of ethanol and 30.6 ml of pyridine was dissolved 2.5 g of (S)-3-(4-(2-(imidazol-1-yl)pyridin-5-yl)-3-fluorophenyl)-2-oxo-5-oxazolidinylmethyl acetamide. The solution was added with 2.36 g of hydroxylamine at room temperature and stirred for 10 hours at the temperature 100° C. The reaction mixture was extracted with ethyl acetate and the organic layer, thus separated, was washed with water and brine. The organic layer was dehydrated, filtered and concentrated in vacuo. The residue, obtained by concentrating, was purified by column chromatography and then dissolved in tetrahydrofuran solution, saturated hydrochloric acid, and stirred for 10 minutes. The solid, prepared by the above reaction, was recrystallized to provide the title compound 1 g.

Example 30

Preparation of (S)-3-(4-(4-(4,5-dimethyloxazol-2-yl) phenyl)-3-fluorophenyl)-2-oxo-5-oxazolidinylmethyl acetamide (compound 11)

The same procedure as in Example 1 was conducted, except for adding 4-(4,5-dimethyloxazol-2-yl)-bromobenzene and using (S)-3-(4-trimethylstannyl-3-fluorophenyl)-2-oxo-5-oxazolidinylmethyl acetamide as a starting material, to obtain the title compound.

¹H NMR (DMSO-d₆) δ 8.24 (m, 1H), 7.96 (m, 2H), 7.62 (m, 4H), 7.45 (dd, 1H), 4.78 (m, 1H), 4.16 (t, 1H), 3.79 (dd, 1H), 3.41 (m, 2H), 2.32 (s, 3H), 2.10 (s, 3H), 1.83 (s, 3H)

Example 31

Preparation of (S)-3-(4-(2-(4,5-dimethyloxazol-2-yl) pyridin-5-yl)-3-fluorophenyl)-2-oxo-5-oxazolidinylmethyl acetamide (compound 15)

The same procedure as in Example 1 was conducted, except for adding 4-(4,5-dimethyloxazol-2-yl)-5-bromopyridine and using (S)-3-(4-trimethylstannyl-3-fluorophenyl)-2-oxo-5-oxazolidinylmethyl acetamide as a starting material, to obtain the title compound.

¹H NMR (DMSO-d₆) δ 8.81 (s, 1H), 8.24 (t, 1H), 8.07 (m, 2H), 7.77 (t, 1H), 7.62 (dd, 1H), 7.45 (dd, 1H), 4.78 (m, 1H), 4.18 (t, 1H), 3.79 (dd, 1H), 3.42 (m, 2H), 2.35 (s, 3H), 2.12 (s, 3H), 1.84 (s, 3H)

Example 32

Preparation of (S)-3-(4-(2-([1,2,3]triazol-2-yl)pyridin-5-yl)-3-fluorophenyl)-2-oxo-5-oxazolidinylmethyl acetamide (compound 25)

The same procedure as in Example 1 was conducted, except for adding 2-([1,2,3]triazol-2-yl)-5-bromopyridine and using (S)-3-(4-trimethylstannyl-3-fluorophenyl)-2-oxo-5-oxazolidinylmethyl acetamide as a starting material, to obtain the title compound.

¹H NMR (DMSO-d₆) δ 8.74 (s, 1H), 8.24 (m, 2H), 8.19 (s, 2H), 8.11 (d, 1H), 7.72 (t, 1H), 7.64 (dd, 1H), 7.45 (dd, 1H), 4.79 (m, 1H), 4.18 (t, 1H), 3.79 (dd, 1H), 3.43 (m, 2H), 1.84 (s, 3H)

Example 33

Preparation of (S)-3-(4-(4-(4(S)-hydroxymethyl-4,5-dihydrooxazol-2-yl)phenyl)-3-fluorophenyl)-2-oxo-5-oxazolidinylmethyl acetamide (compound 26)

The same procedure as in Example 1 was conducted, except for adding 4-(4(S)-hydroxymethyl-4,5-dihydrooxazol-2-yl)-bromobenzene and using (S)-3-(4-trimethylstannyl-3-fluorophenyl)-2-oxo-5-oxazolidinylmethyl acetamide as a starting material, to obtain the title compound.

¹H NMR (DMSO-d₆) δ 8.23 (t, 1H), 7.91 (d, 2H), 7.62 (m, 4H), 7.42 (dd, 1H), 4.82 (t, 1H), 4.78 (m, 1H), 4.41 (t, 1H), 4.28 (m, 2H), 4.16 (t, 1H), 3.79 (dd, 1H), 3.61 (m, 1H), 3.48 (m, 1H), 3.43 (m, 2H), 1.84 (s, 3H)

Example 34

Preparation of (S)-3-(4-(4-(4-cyanomethyl thiazol-2-yl)phenyl)-3-fluorophenyl)-2-oxo-5-oxazolidinylmethyl acetamide (compound 31)

The same procedure as in Example 1 was conducted, except for adding 4-(4-cyanomethyl thiazol-2-yl)-bromobenzene and using (S)-3-(4-trimethylstannyl-3-fluorophenyl)-2-oxo-5-oxazolidinylmethyl acetamide as a starting material, to obtain the title compound.

¹H NMR (DMSO-d₆) δ 8.25 (t, 1H), 8.00 (d, 2H), 7.67 (m, 4H), 7.44 (dd, 1H), 4.79 (m, 1H), 4.23 (s, 2H), 4.14 (t, 1H), 3.79 (dd, 1H), 3.43 (m, 2H), 1.83 (s, 3H)

Example 35

Preparation of (R)-3-(4-(4-(4-hydroxymethyl thiazol-2-yl)phenyl)-3-fluorophenyl)-5-([1,2,3]triazol-1-yl)methyl oxazolidin-2-one (compound 36)

The same procedure as in Example 1 was conducted, except for adding 4-(4-hydroxymethyl thiazol-2-yl)-bromobenzene and using (R)-3-(4-trimethylstannyl-3-fluorophenyl)-5-[1,2,3]triazol-1-yl oxazolidin-2-one as a starting material, to obtain the title compound.

¹H NMR (DMSO-d₆) δ 8.16 (s, 1H), 8.00 (d, 2H), 7.75 (s, 1H), 7.64 (dd, 2H), 7.62 (t, 1H), 7.52 (dd, 1H), 7.48 (s, 1H), 7.36 (dd, 1H), 5.40 (t, 1H), 5.18 (m, 1H), 4.85 (d, 2H), 4.62 (d, 2H), 4.28 (t, 1H), 3.95 (dd, 1H)

Example 36

Preparation of (R)-3-(4-(4-(4-glycyloxymethyl thiazol-2-yl)phenyl)-3-fluorophenyl)-5-([1,2,3]triazol-1-yl)methyl oxazolidin-2-one trifluoroacetic acid (compound 37)

The same procedure as in Example 10 was conducted, except for using (R)-3-(4-(4-(4-hydroxymethyl thiazol-2-yl) phenyl)-3-fluorophenyl)-5-[1,2,3]triazol-1-ylmethyl oxazolidin-2-one as a starting material, to obtain the title compound.

$^1$H NMR (DMSO-d$_6$) δ 8.29 (s, 3H), 8.17 (s, 1H), 8.00 (d, 2H), 7.85 (s, 1H), 7.75 (s, 1H), 7.69 (dd, 2H), 7.67 (t, 1H), 7.55 (dd, 1H), 7.43 (dd, 1H), 5.36 (s, 2H), 5.19 (m, 1H), 4.86 (d, 2H), 4.28 (t, 1H), 4.28 (t, 1H)

Example 37

Preparation of (R)-3-(4-(2-(2-methyltetrazol-5-yl) pyridin-5-yl)-3-fluorophenyl)-5-methoxymethyl oxazolidin-2-one (compound 33)

In 10 ml of methanol was dissolved 400 mg of (R)-3-(4-(2-(2-methyltetrazol-5-yl)pyridin-5-yl)-3-fluorophenyl)-5-methansulfonyloxymethyl oxazolidin-2-one prepared in the secondary step of the Example 24. The solution was added with 90 mg of sodiummethoxide at room temperature and then stirred for one day at room temperature. The solution was extracted with ethyl acetate and the organic layer, thus separated, was washed with water and brine. The organic layer was dehydrated, filtered, concentrated in vacuo and purified by column chromatography to provide the title compound 200 mg. Yield 58%.

$^1$H NMR (CDCl$_3$) δ 8.90 (s, 1H), 8.29 (d, 1H), 8.04 (d, 1H), 7.61 (dd, 1H), 7.58 (t, 1H), 7.38 (dd, 1H), 4.80 (m, 1H), 4.45 (s, 3H), 4.08 (t, 1H), 3.96 (dd, 1H), 3.67 (m, 2H), 3.43 (s, 3H)

Example 38

Preparation of (R)-3-(4-(2-(2-methyltetrazol-5-yl) pyridin-5-yl)-3-fluorophenyl)-5-(N,N-dimethylaminomethyl)oxazolidin-2-one (compound 40)

In 5 ml of dimethylformamide was dissolved 100 mg of (R)-3-(4-(2-(2-methyltetrazol-5-yl)pyridin-5-yl)-3-fluorophenyl)-5-methanesulfonyloxymethyl oxazolidin-2-one prepared in the secondary step of the Example 24. The solution was added with 30 mg of dimethylamine hydrochloride at room temperature. The solution was stirred for 30 hours at the temperature of 60° C. And then the solution was extracted with ethyl acetate and the organic layer, thus separated, was washed with water and brine. The residue, prepared by dehydrating, filtering and concentrating the organic layer, was purified by column chromatography to provide the title compound 70 mg. Yield 76%.

$^1$H NMR (DMSO-d$_6$) δ 8.91 (s, 1H), 8.19 (m, 2H), 7.76 (t, 1H), 7.65 (dd, 1H), 7.49 (dd, 1H), 4.98 (m, 1H), 4.63 (s, 3H), 4.27 (m, 3H), 3.94 (dd, 1H), 2.79 (s, 3H), 2.74 (s, 3H)

Example 39

Preparation of (S)-3-(4-(2-(2-methyltetrazol-5-yl) pyridin-5-yl)-3-fluorophenyl)-5-N-methylaminomethyl oxazolidin-2-one (compound 41)

In 7 ml of dimethylformamide was dissolved 200 mg of (R)-3-(4-(2-(2-methyltetrazol-5-yl)pyridin-5-yl)-3-fluorophenyl)-5-methanesulfonyloxymethyl oxazolidin-2-one, prepared in the primary step of the Example 24. The solution was added with 100 mg of methylamine hydrochloride and 240 mg of potassiumcarbonate at room temperature. The solution was stirred for 30 hours at the temperature of 80° C. The solution was added with ethyl acetate and then the organic layer, thus separated, was washed with water and brine. The residue, prepared by dehydrating, filtering and concentrating the organic layer, was purified by column chromatography to obtain the title compound 80 mg. Yield 45%.

$^1$H NMR (DMSO-d$_6$) δ 8.91 (s, 1H), 8.18 (m, 2H), 7.73 (t, 1H), 7.66 (dd, 1H), 7.47 (dd, 1H), 7.17 (m, 1H), 4.94 (m, 1H), 4.46 (s, 3H), 4.25 (m, 3H), 3.85 (dd, 1H), 2.49 (d, 3H)

Example 40

Preparation of (R)-3-(4-(2-(2-methyltetrazol-5-yl) pyridin-5-yl)-3-fluorophenyl)-5-(L-alanyloxy)methyl oxazolidin-2-one trifluoroacetic acid (compound 42)

The same procedure as in Example 10 was carried out to provide the title compound using BOC-L-alanine instead of BOC-glycine.

$^1$H NMR (DMSO-d$_6$) δ 8.91 (s, 1H), 8.42 (s, 3H), 8.20 (m, 2H), 7.75 (t, 1H), 7.67 (dd, 1H), 7.48 (dd, 1H), 5.05 (m, 1H), 4.61 (dd, 1H), 4.46 (s, 3H), 4.41 (dd, 1H), 4.26 (t, 1H), 4.18 (m, 1H), 3.96 (dd, 1H), 1.36 (d, 3H)

Example 41

Preparation of (R)-3-(4-(2-(2-methyltetrazol-5-yl) pyridin-5-yl)-3-fluorophenyl)-5-(L-valyloxy)methyl oxazolidin-2-one hydrochloride (compound 43)

500 mg of compound 20, prepared in Example 11, was dissolved in water. The solution was controlled to pH 5 with the addition of sodium bicarbonate aqueous solution. The aqueous layer was extracted with ethyl acetate and then the organic layer was slowly added with ether solution saturating of hydrochloric acid. The solid prepared by the above method was filtered and concentrated in vacuo to provide the title compound 200 mg. Yield 46%.

$^1$H NMR (DMSO-d$_6$) δ 8.92 (s, 1H), 8.54 (bs, 3H), 8.20 (m, 2H), 7.76 (t, 1H), 7.65 (dd, 1H), 7.49 (dd, 1H), 5.04 (m, 1H), 4.58 (dd, 1H), 4.46 (s, 3H), 4.41 (dd, 1H), 4.26 (t, 1H), 3.95 (m, 2H), 2.17 (m, 1H), 0.97 (d, 3H), 0.94 (d, 3H)

Example 42

Preparation of (R)-3-(4-(2-(2-methyltetrazol-5-yl) pyridin-5-yl)-3-fluorophenyl)-5-(L-alanyloxy)methyl oxazolidin-2-one hydrochloride (compound 44)

With the exception of using compound 42, the same procedure as in Example 41 was conducted to prepare the title compound.

$^1$H NMR (DMSO-d$_6$) δ 8.92 (s, 1H), 8.52 (bs, 3H), 8.20 (m, 2H), 7.75 (t, 1H), 7.66 (dd, 1H), 7.49 (dd, 1H), 5.05 (m, 1H), 4.60 (dd, 1H), 4.46 (s, 3H), 4.41 (dd, 1H), 4.26 (t, 1H), 4.18 (m, 1H), 4.00 (dd, 1H), 1.37 (d, 3H)

Example 43

Preparation of (R)-3-(4-(2-(2-methyltetrazol-5-yl) pyridin-5-yl)-3-fluorophenyl)-5-glycyloxymethyl oxazolidin-2-one hydrochloride (compound 45)

With the exception of using the compound 12, the same procedure as in Example 41 was conducted to prepare the title compound.
$^1$H NMR (DMSO-d$_6$) δ 8.91 (s, 1H), 8.48 (bs, 3H), 8.18 (m, 2H), 7.75 (t, 1H), 7.65 (dd, 1H), 7.49 (dd, 1H), 5.03 (m, 1H), 4.48 (m, 2H), 4.46 (s, 3H), 4.24 (t, 1H), 3.99 (dd, 1H), 3.86 (m, 2H)

Example 44

Preparation of (S)-3-(4-(4-(4-hydroxymethylthiazol-2-yl)phenyl)-3-fluorophenyl)-2-oxo-5-oxazolidinylmethyl acetamide (compound 28)

With the exception of using (S)-3-(4-trimethylstannyl-3-fluorophenyl)-2-oxo-5-oxazolidinylmethyl acetamide as a starting material and 4-(4-hydroxymethylthiazol-2-yl)-bromobenzene, the same procedure as in Example 1 was conducted to prepare the title compound.
$^1$H NMR (DMSO-d$_6$) δ 8.24 (t, 1H), 7.98 (d, 2H), 7.65 (m, 2H), 7.59 (m, 2H), 7.43 (s, 1H), 7.41 (dd, 1H), 5.40 (t, 1H), 4.79 (m, 1H), 4.63 (d, 2H), 4.16 (t, 1H), 3.79 (dd, 1H), 3.43 (m, 2H), 1.84 (s, 3H)

Example 45

(R)-3-(4-(2-(2-methyltetrazol-5-yl)pyridin-5-yl)-3-fluorophenyl)-5-(L-prolinyloxy)methyl oxazolidin-2-one trifluoroacetic acid (compound 46)

With the exception of using BOC-L-proline, instead of BOC-glycine, the same procedure as in Example 10 was conducted to prepare the title compound.
$^1$H NMR (DMSO-d$_6$) δ 9.25 (bs, 2H), 8.91 (s, 1H), 8.20 (m, 2H), 7.76 (t, 1H), 7.65 (dd, 1H), 7.48 (dd, 1H), 5.05 (m, 1H), 4.57 (dd, 1H), 4.45 (s, 3H), 4.41 (dd, 1H), 4.26 (t, 1H), 3.96 (dd, 1H), 3.23 (m, 2H), 2.21 (m, 1H), 1.92 (m, 3H)

Example 46

Preparation of (R)-3-(4-(2-(2-methyltetrazol-5-yl) pyridin-5-yl)-3-fluorophenyl)-5-(L-prolinyloxy)methyl oxazolidin-2-one hydrochloride (compound 47)

With the exception of using the compound 46, the same procedure as in Example 41 was conducted to prepare the title compound.
$^1$H NMR (DMSO-d$_6$) δ 9.11 (bs, 2H), 8.91 (s, 1H), 8.20 (m, 2H), 7.76 (t, 1H), 7.65 (dd, 1H), 7.49 (dd, 1H), 5.05 (m, 1H), 4.55 (dd, 1H), 4.46 (s, 3H), 4.41 (dd, 1H), 4.25 (t, 1H), 4.01 (dd, 1H), 3.36 (m, 2H), 2.07 (m, 1H), 1.89 (m, 3H)

Example 47

Preparation of (R)-3-(4-(2-(2-methyl-[1,3,4]oxadiazol-5-yl)pyridin-5-yl)-3-fluorophenyl)-5-glycyloxymethyl oxazolidin-2-one hydrochloride (compound 48)

With the exception of using the compound 27, the same procedure as in Example 41 was conducted to prepare the title compound.
$^1$H NMR (DMSO-d$_6$) δ 8.92 (s, 1H), 8.48 (s, 3H), 8.21 (s, 2H), 7.76 (t, 1H), 7.66 (dd, 1H), 7.48 (dd, 1H), 5.04 (m, 1H), 4.47 (m, 2H), 4.23 (t, 1H), 3.94 (m, 1H), 3.84 (d, 2H), 2.62 (s, 3H)

Example 48

Preparation of (R)-3-(4-(2-(2-methyltetrazol-5-yl) pyridin-5-yl)-3-fluorophenyl)-5-(β-alanyloxy)methyl oxazolidin-2-one trifluoroacetic acid (compound 49)

With the exception of using BOC-β-alanine, instead of BOC-glycine, the same procedure as in Example 10 was conducted to prepare the title compound.
$^1$H NMR (DMSO-d$_6$) δ 8.91 (s, 1H), 8.20 (m, 2H), 7.75 (t, 1H), 7.73 (bs, 3H), 7.68 (dd, 1H), 7.48 (dd, 1H), 5.02 (m, 1H), 4.46 (s, 3H), 4.36 (m, 2H), 4.26 (t, 1H), 3.93 (dd, 1H), 3.02 (m, 2H), 2.70 (t, 2H)

Example 49

Preparation of (R)-3-(4-(2-(2-methyltetrazol-5-yl) pyridin-5-yl)-3-fluorophenyl)-5-(β-alanyloxy)methyl oxazolidin-2-one hydrochloride (compound 50)

With the exception of using the compound 49, the same procedure as in Example 41 was conducted to prepare the title compound.
$^1$H NMR (DMSO-d$_6$) δ 8.91 (s, 1H), 8.22 (m, 2H), 8.11 (bs, 3H), 7.76 (t, 1H), 7.65 (dd, 1H), 7.48 (dd, 1H), 5.02 (m, 1H), 4.46 (s, 3H), 4.36 (m, 2H), 4.23 (t, 1H), 3.95 (m, 1H), 3.00 (m, 2H), 2.74 (t, 2H)

Example 50

Preparation of (R)-3-(4-(2-(2-methyl-[1,3,4]oxadiazol-5-yl)pyridin-5-yl)-3-fluorophenyl)-5-(L-alanyloxy)methyl oxazolidin-2-one trifluoroacetic acid (compound 51)

With the exception of using the compound 16 and BOC-L-alanine, the same procedure as in Example 10 was conducted to prepare the title compound:
$^1$H NMR (DMSO-d$_6$) δ 8.93 (s, 1H), 8.39 (bs, 3H), 8.21 (s, 2H), 7.76 (t, 1H), 7.68 (dd, 1H), 7.49 (dd, 1H), 5.04 (m, 1H), 4.61 (dd, 1H), 4.40 (dd, 1H), 4.28 (t, 1H), 4.18 (dd, 1H), 3.95 (dd, 1H), 2.62 (s, 3H), 1.36 (d, 3H)

Example 51

Preparation of (R)-3-(4-(2-(2-methyl-[1,3,4]oxadiazol-5-yl)pyridin-5-yl)-3-fluorophenyl)-5-(L-alanyloxy)methyl oxazolidin-2-one hydrochloride (compound 52)

With the exception of using the compound 51, the same procedure as in Example 41 was conducted to prepare the title compound.

¹H NMR (DMSO-d₆) δ 8.93 (s, 1H), 8.61 (bs, 3H), 8.21 (s, 2H), 7.76 (t, 1H), 7.65 (dd, 1H), 7.49 (dd, 1H), 5.05 (m, 1H), 4.58 (dd, 1H), 4.39 (dd, 1H), 4.25 (t, 1H), 4.12 (m, 1H), 4.00 (dd, 1H), 2.62 (s, 3H), 1.36 (d, 3H)

Example 52

Preparation of (R)-3-(4-(2-(2-methyl-[1,3,4]oxadiazol-5-yl)pyridin-5-yl)-3-fluorophenyl)-5-(L-valyloxy)methyl oxazolidin-2-one trifluoroacetic acid (compound 53)

With the exception of using the compound 16 and BOC-L-valine, the same procedure as in Example 10 was conducted to prepare the title compound.
¹H NMR (DMSO-d₆) δ 8.93 (s, 1H), 8.40 (bs, 3H), 8.21 (s, 2H), 7.75 (t, 1H), 7.68 (dd, 1H), 7.48 (dd, 1H), 5.04 (m, 1H), 4.62 (dd, 1H), 4.40 (dd, 1H), 4.26 (t, 1H), 3.99 (d, 1H), 3.92 (dd, 1H), 2.62 (s, 3H), 2.12 (m, 1H), 0.97 (d, 3H), 0.94 (d, 3H)

Example 53

Preparation of (R)-3-(4-(2-(2-methyl-[1,3,4]oxadiazol-5-yl)pyridin-5-yl)-3-fluorophenyl)-5-(L-valyloxy)methyl oxazolidin-2-one hydrochloride (compound 54)

With the exception of using the compound 53, the same procedure as in Example 41 was conducted to prepare the title compound.
¹H NMR (DMSO-d₆) δ 8.93 (s, 1H), 8.60 (bs, 3H), 8.21 (s, 2H), 7.75 (t, 1H), 7.67 (dd, 1H), 7.49 (dd, 1H), 5.04 (m, 1H), 4.58 (dd, 1H), 4.42 (dd, 1H), 4.26 (t, 1H), 3.92 (m, 1H), 2.62 (s, 3H), 2.12 (m, 1H), 0.97 (d, 3H), 0.94 (d, 3H)

Example 54

Preparation of (R)-3-(4-(2-(2-methyl-[1,3,4]oxadiazol-5-yl)pyridin-5-yl)-3-fluorophenyl)-5-(L-prolinyloxy)methyl oxazolidin-2-one trifluoroacetic acid (compound 55)

With the exception of using the compound 16 and BOC-L-proline, the same procedure as in Example 10 was conducted to prepare the title compound.
¹H NMR (DMSO-d₆) δ 9.20 (bs, 2H), 8.93 (s, 1H), 8.21 (s, 2H), 7.77 (t, 1H), 7.66 (dd, 1H), 7.50 (dd, 1H), 5.04 (m, 1H), 4.59 (dd, 1H), 4.43 (m, 2H), 4.26 (t, 1H), 3.96 (dd, 1H), 3.21 (m, 2H), 2.62 (s, 3H), 2.21 (m, 1H), 1.95 (m, 1H), 1.89 (m, 2H)

Example 55

Preparation of (R)-3-(4-(2-(2-methyl-[1,3,4]oxadiazol-5-yl)pyridin-5-yl)-3-fluorophenyl)-5-(L-prolinyloxy)methyl oxazolidin-2-one hydrochloride (compound 56)

With the exception of using the compound 55, the same procedure as in Example 41 was conducted to prepare the title compound.
¹H NMR (DMSO-d₆) δ 9.18 (bs, 2H), 8.93 (s, 1H), 8.21 (s, 2H), 7.76 (t, 1H), 7.65 (dd, 1H), 7.49 (dd, 1H), 5.05 (m, 1H), 4.57 (dd, 1H), 4.43 (m, 2H), 4.26 (t, 1H), 4.00 (dd, 1H), 3.21 (m, 2H), 2.62 (s, 3H), 2.21 (m, 1H), 1.95 (m, 1H), 1.89 (m, 2H)

Example 56

Preparation of (R)-3-(4-(2-(2-methyl-[1,3,4]oxadiazol-5-yl)pyridin-5-yl)-3-fluorophenyl)-5-(β-alanyloxy)methyl oxazolidin-2-one trifluoroacetic acid (compound 57)

With the exception of using the compound 16 and BOC-β-alanine, the same procedure as in Example 10 was conducted to prepare the title compound.
¹H NMR (DMSO-d₆) δ 8.92 (s, 1H), 8.21 (s, 2H), 7.88 (bs, 3H), 7.76 (t, 1H),
7.68 (dd, 1H), 7.49 (dd, 1H), 5.02 (m, 1H), 4.36 (m, 2H), 4.25 (t, 1H), 3.94 (dd, 1H), 3.03 (m, 2H), 2.70 (t, 2H), 2.62 (s, 3H)

Example 57

Preparation of (R)-3-(4-(2-(2-methyl-[1,3,4]oxadiazol-5-yl)pyridin-5-yl)-3-fluorophenyl)-5-(β-alanyloxy)methyl oxazolidin-2-one hydrochloride (compound 58)

With the exception of using the compound 57, the same procedure as in Example 41 was conducted to prepare the title compound.
¹H NMR (DMSO-d₆) δ 8.92 (s, 1H), 8.21 (s, 2H), 8.08 (bs, 3H), 7.76 (t, 1H), 7.68 (dd, 1H), 7.49 (dd, 1H), 5.02 (m, 1H), 4.36 (m, 2H), 4.25 (t, 1H), 3.96 (dd, 1H), 3.00 (m, 2H), 2.71 (t, 2H), 2.62 (s, 3H)

Example 58

Preparation of mono-[(R)-[3-(4-(2-(2-methyltetrazol-5-yl)pyridin-5-yl)-3-fluorophenyl)-2-oxo-5-oxazolidinyl]methyl]phosphate (compound 72) and (R)-[3-(4-(2-(2-methyltetrazol-5-yl)pyridin-5-yl)-3-fluorophenyl)-2-oxo-5-oxazolidinyl]methyl disodiumphosphate (compound 59)

1. The Primary Step
In 10 ml of mixture solvent (tetrahydrofuran:methylene chloride=1:1) was dissolved 1 g of compound 10. The solution was added with 0.6 g of tetrazole and 2.3 g of di-tetrabutyl diisopropylphosphoamidite and stirred for 15 hours at room temperature. The reaction mixture was refrigerated to −78° C., added with 0.7 g of metachloroperbenzoic acid and stirred for 2 hours. After being cooling to −78° C., the reaction mixture was added with metachloroperbenzoic acid (0.7 g). When the reaction mixture was stirred for 2 hours, the temperature of the reaction mixture was raised to room temperature. The reaction mixture was then added with ethyl acetate. The organic layer, thus separated, was washed with sodiumbisulfate, sodiumbicarbonate and brine, dehydrated, filtered and concentrated in vacuo, followed by purification with column chromatography thereby to provide (R)-[3-(4-(2-(2-methyltetrazol-5-yl)pyridin-5-yl)-3-fluorophenyl)-2-oxo-5-oxazolidinyl]methyl phosphoric acid ditetrabuthylester (0.71 g, 71%).
¹H NMR (DMSO-d₆) δ 8.90 (s, 1H), 8.18 (m, 2H), 7.74 (t, 1H), 7.68 (dd, 1H), 7.49 (dd, 1H), 4.98 (m, 1H), 4.46 (s, 3H), 4.23 (t, 1H), 4.18 (m, 1H), 4.09 (m, 1H), 3.89 (dd, 1H), 1.39 (s, 9H), 1.38 (s, 9H)
The crystal prepared the above method was dissolved in a mixture of methanol and chloroform. And then the solution added with 3.4 ml of sodiummethoxide (0.3M methanol solution) at the room temperature and stirred for 10 hours. The reaction mixture was concentrated to prepare the residue. The residue was crystallized and filtered thereby to obtain the title compound (compound 59) 300 mg.

$^1$H NMR (D$_2$O) δ 8.27 (s, 1H), 7.56 (dd, 2H), 7.06 (m, 2H), 6.90 (m, 1H), 4.79 (m, 1H), 4.63 (s, 3H), 3.90 (m, 4H)

2. The Secondary Step

In 30 ml of methylene chloride was dissolved the compound (0.7 g) in the Primary Step. The solution was added with 15 ml of trifluoroacetic acid and then stirred for 1 hour at room temperature. The reaction mixture was concentrated in vacuo to prepare the residue. The residue was crystallized with ethanol and ethyl ether to obtain mono-[(R)-[3-(4-(2-(2-methyltetrazol-5-yl)pyridin-5-yl)-3-fluorophenyl)-2-oxo-5-oxazolidinyl]methyl]phosphate (compound 72) 400 mg.

$^1$H NMR (DMSO-d$_6$) δ 8.92 (s, 1H), 8.20 (m, 2H), 7.74 (t, 1H), 7.66 (dd, 1H), 7.50 (dd, 1H), 4.95 (m, 1H), 4.46 (s, 3H), 4.21 (t, 1H), 4.05 (m, 2H), 3.91 (dd, 1H)

Example 59

Preparation of (R)-[3-(4-(2-(2-methyl-[1,3,4]oxadiazol-5-yl)pyridin-5-yl)-3-fluorophenyl)-2-oxo-5-oxazolidinyl]methyl disodiumphosphate (compound 60)

Using the compound 16, the title compound was prepared in a manner similar to that of the Example 58.

$^1$H NMR (D$_2$O) δ 8.33 (s, 1H), 7.65 (dd, 2H), 7.17 (m, 2H), 6.90 (m, 1H), 4.79 (m, 1H), 4.63 (s, 3H), 3.94 (t, 1H), 3.78 (m, 3H)

Example 60

Preparation of (R)-3-(4-(2-(1-methyltetrazol-5-yl) pyridin-5-yl)-3-fluorophenyl)-5-hydroxymethyl oxazolidin-2-one (compound 61)

Using 2-(1-methyltetrazol-5-yl)-5-bromopyridine, the title compound was prepared in a manner similar to that of the Example 1.

$^1$H NMR (DMSO-d$_6$) δ 8.98 (s, 1H), 8.30 (m, 2H), 7.75 (m, 2H), 7.53 (dd, 1H), 5.25 (t, 1H), 4.76 (m, 1H), 4.44 (s, 3H), 4.14 (t, 1H), 3.89 (dd, 1H), 3.69 (m, 1H), 3.58 (m, 1H)

Example 61

Preparation of (R)-3-(4-(2-(1-methyltetrazol-5-yl) pyridin-5-yl)-3-fluorophenyl)-5-glycyloxymethyl oxazolidin-2-one trifluoroacetic acid (compound 62)

Using 2-(1-methyltetrazol-5-yl)-5-bromopyridine, the title compound was prepared in a manner similar to that of the Example 10.

$^1$H NMR (DMSO-d$_6$) δ 8.95 (s, 1H), 8.20 (s, 3H), 8.19 (m, 2H), 7.80 (t, 1H), 7.69 (dd, 1H), 7.49 (dd, 1H), 5.00 (m, 1H), 4.46 (m, 2H), 4.45 (s, 3H), 4.24 (t, 1H), 3.92 (dd, 1H), 3.90 (s, 2H)

Example 62

Preparation of (R)-3-(4-(2-(1-methyltetrazol-5-yl) pyridin-5-yl)-3-fluorophenyl)-5-glycyloxymethyl oxazolidin-2-one hydrochloride (compound 63)

Using 2-(1-methyltetrazol-5-yl)-5-bromopyridine, the title compound was prepared in a manner similar to that of the Example 43.

$^1$H NMR (DMSO-d$_6$) δ 8.95 (s, 1H), 8.50 (bs, 3H), 8.21 (m, 2H), 7.80 (t, 1H), 7.65 (dd, 1H), 7.49 (dd, 1H), 5.03 (m, 1H), 4.48 (m, 2H), 4.43 (s, 3H), 4.24 (t, 1H), 3.99 (dd, 1H), 3.86 (m, 2H)

Example 63

Preparation of (R)-3-(4-(2-(1-methyltetrazol-5-yl) pyridin-5-yl)-3-fluorophenyl)-5-(L-alanyloxy)methyl oxazolidin-2-one trifluoroacetic acid (compound 64)

Using 2-(1-methyltetrazol-5-yl)-5-bromopyridine, the title compound was prepared in a manner similar to that of the Example 40.

$^1$H NMR (DMSO-d$_6$) δ 8.95 (s, 1H), 8.43 (s, 3H), 8.25 (m, 2H), 7.77 (t, 1H), 7.68 (dd, 1H), 7.48 (dd, 1H), 5.05 (m, 1H), 4.63 (dd, 1H), 4.44 (s, 3H), 4.42 (dd, 1H), 4.24 (t, 1H), 4.18 (m, 1H), 3.98 (dd, 1H), 1.36 (d, 3H)

Example 64

Preparation of (R)-3-(4-(2-(1-methyltetrazol-5-yl) pyridin-5-yl)-3-fluorophenyl)-5-(L-alanyloxy)methyl oxazolidin-2-one hydrochloride (compound 65)

Using 2-(1-methyltetrazol-5-yl)-5-bromopyridine, the title compound was prepared in a manner similar to that of the Example 42.

$^1$H NMR (DMSO-d$_6$) δ 8.95 (s, 1H), 8.53 (bs, 3H), 8.24 (m, 2H), 7.77 (t, 1H), 7.67 (dd, 1H), 7.49 (dd, 1H), 5.05 (m, 1H), 4.60 (dd, 1H), 4.43 (s, 3H), 4.42 (dd, 1H), 4.26 (t, 1H), 4.20 (m, 1H), 4.00 (dd, 1H), 1.37 (d, 3H)

Example 65

Preparation of (R)-3-(4-(2-(1-methyltetrazol-5-yl) pyridin-5-yl)-3-fluorophenyl)-5-(L-valyloxy)methyl oxazolidin-2-one trifluoroacetic acid (compound 66)

Using 2-(1-methyltetrazol-5-yl)-5-bromopyridine, the title compound was prepared in a manner similar to that of the Example 11.

$^1$H NMR (DMSO-d$_6$) δ 8.95 (s, 1H), 8.42 (s, 3H), 8.25 (m, 2H), 7.79 (t, 1H), 7.70 (dd, 1H), 7.48 (dd, 1H), 5.05 (m, 1H), 4.64 (dd, 1H), 4.44 (s, 3H), 4.43 (dd, 1H), 4.30 (t, 1H), 4.01 (d, 1H), 3.93 (dd, 1H), 2.14 (m, 1H), 0.98 (d, 3H), 0.95 (d, 3H)

Example 66

Preparation of (R)-3-(4-(2-(1-methyltetrazol-5-yl) pyridin-5-yl)-3-fluorophenyl)-5-(L-valyloxy)methyl oxazolidin-2-one hydrochloride (compound 67)

Using 2-(1-methyltetrazol-5-yl)-5-bromopyridine, the title compound was prepared in a manner similar to that of the Example 41.

$^1$H NMR (DMSO-d$_6$) δ 8.94 (s, 1H), 8.57 (bs, 3H), 8.22 (m, 2H), 7.79 (t, 1H), 7.67 (dd, 1H), 7.49 (dd, 1H), 5.04 (m, 1H), 4.59 (dd, 1H), 4.43 (s, 3H), 4.41 (dd, 1H), 4.27 (t, 1H), 3.99 (m, 2H), 2.17 (m, 1H), 0.97 (d, 3H), 0.94 (d, 3H)

Example 67

Preparation of (R)-3-(4-(2-(1-methyltetrazol-5-yl) pyridin-5-yl)-3-fluorophenyl)-5-(β-alanyloxy)methyl oxazolidin-2-one trifluoroacetic acid (compound 68)

Using 2-(1-methyltetrazol-5-yl)-5-bromopyridine, the title compound was prepared in a manner similar to that of the Example 48.

¹H NMR (DMSO-d₆) δ 8.94 (s, 1H), 8.24 (m, 2H), 7.77 (t, 1H), 7.73 (bs, 3H), 7.70 (dd, 1H), 7.49 (dd, 1H), 5.02 (m, 1H), 4.44 (s, 3H), 4.36 (m, 2H), 4.27 (t, 1H), 3.93 (dd, 1H), 3.05 (m, 2H), 2.70 (t, 2H)

Example 68

Preparation of (R)-3-(4-(2-(1-methyltetrazol-5-yl) pyridin-5-yl)-3-fluorophenyl)-5-(β-alanyloxy)methyl oxazolidin-2-one hydrochloride (compound 69)

Using 2-(1-methyltetrazol-5-yl)-5-bromopyridine, the title compound was prepared in a manner similar to that of the Example 49.
¹H NMR (DMSO-d₆) δ 8.96 (s, 1H), 8.25 (m, 2H), 8.13 (bs, 3H), 7.79 (t, 1H), 7.66 (dd, 1H), 7.48 (dd, 1H), 5.02 (m, 1H), 4.43 (s, 3H), 4.36 (m, 2H), 4.25 (t, 1H), 3.97 (m, 1H), 3.01 (m, 2H), 2.74 (t, 2H)

Example 69

Preparation of mono-[(R)-[3-(4-(2-(1-methyltetrazol-5-yl)pyridin-5-yl)-3-fluorophenyl)-2-oxo-5-oxazolidinyl]methyl]phosphate (compound 73) and (R)-[3-(4-(2-(1-methyltetrazol-5-yl)pyridin-5-yl)-3-fluorophenyl)-2-oxo-5-oxazolidinyl]methyl disodiumphosphate (compound 70)

1. The Primary Step
Using the compound 61, (R)-[3-(4-(2-(1-methyltetrazol-5-yl)pyridin-5-yl)-3-fluorophenyl)-2-oxo-5-oxazolidinyl]methyl phosphoric acid ditetrabutylester was prepared in a manner similar to that of the Example 58.
¹H NMR (DMSO-d₆) δ 8.94 (s, 1H), 8.20 (m, 2H), 7.78 (t, 1H), 7.68 (dd, 1H), 7.49 (dd, 1H), 4.98 (m, 1H), 4.44 (s, 3H), 4.21 (t, 1H), 4.18 (m, 1H), 4.10 (m, 1H), 3.89 (dd, 1H), 1.39 (s, 9H), 1.38 (s, 9H)

2. The Secondary Step
Using the compound provided in the Primary Step, 400 mg of mono-[(R)-[3-(4-(2-(1-methyltetrazol-5-yl)pyridin-5-yl)-3-fluorophenyl)-2-oxo-5-oxazolidinyl]methyl]phosphate (compound 73) was prepared in a manner similar to that of the Example 58.
¹H NMR (DMSO-d₆) δ 8.95 (s, 1H), 8.23 (m, 2H), 7.76 (t, 1H), 7.66 (dd, 1H), 7.500 (dd, 1H), 4.95 (m, 1H), 4.44 (s, 3H), 4.21 (t, 1H), 4.05 (m, 2H), 3.91 (dd, 1H)

The title compound (compound 70) was obtained in a manner similar to that of the Example 58.
¹H NMR (D₂O) δ 8.29 (s, 1H), 7.60 (dd, 2H), 7.10 (m, 2H), 6.90 (m, 1H), 4.79 (m, 1H), 4.60 (s, 3H), 3.90 (m, 4H)

Example 70

Preparation of (R)-3-(4-(2-(1-methyltetrazol-5-yl) pyridin-5-yl)-3-fluorophenyl)-5-([1,2,3]triazol-1-yl) methyl oxazolidin-2-one (compound 71)

Using the compound 61, the title compound was prepared in a manner similar to that of the Example 24.
¹H NMR (DMSO-d₆) δ 8.95 (s, 1H), 8.21 (m, 3H), 7.77 (s, 1H), 7.75 (t, 1H), 7.59 (dd, 1H) 7.42 (dd, 1H), 5.22 (m, 1H), 4.86 (m, 2H), 4.44 (s, 3H), 4.31 (t, 1H), 3.98 (dd, 1H)

Experimental Example 1

Assay for In Vitro Antibacterial Activity

To test an antibacterial activity of the derivatives of oxazolidinone, the antibacterial activity, including methicillin resistant *Staphylococcus aureus* (MRSA) and vancomycin resistant Enterococci (VRE), was represented as Minimum Inhibitory Concentration ($MIC_{50}$, μg/ml) using agar dilution described in a art (*Chemotherapy*, 29(1), 76, (1981)). Zyvox of Pharmacia & Upjohn Inc, corresponding to Formula 3, was used as control. The results are shown in Table 2.

TABLE 2

| Compound | Minimum Inhibitory Concentration ($MIC_{50}$, μg/ml) | |
| --- | --- | --- |
| | MRSA | VRE |
| Zyvox | 2 | 2 |
| 1 | 1 | 0.25 |
| 2 | 0.5 | 0.125 |
| 3 | 0.25 | 0.25 |
| 4 | 2 | 2 |
| 5 | 0.5 | 0.25 |
| 6 | NA | NA |
| 7 | 0.5 | 0.5 |
| 8 | 16 | 16 |
| 9 | 0.25 | 0.125 |
| 10 | 0.5 | 0.25 |
| 11 | 0.5 | 0.25 |
| 12 | 0.5 | 0.25 |
| 13 | 0.25 | 0.25 |
| 14 | 0.25 | 0.25 |
| 15 | 1 | 1 |
| 16 | 0.5 | 1 |
| 17 | 1 | 1 |
| 18 | 1 | 2 |
| 19 | 32 | 32 |
| 20 | 0.5 | 0.25 |
| 21 | 1 | 1 |
| 22 | 1 | 1 |
| 23 | 2 | 2 |
| 24 | 0.5 | 0.5 |
| 25 | 0.25 | 0.125 |
| 26 | 0.5 | 0.5 |
| 27 | 0.5 | 1 |
| 28 | 0.5 | 0.5 |
| 29 | 0.5 | 1 |
| 30 | 0.5 | 0.5 |
| 31 | 0.5 | 0.5 |
| 32 | 0.5 | 1 |
| 33 | 2 | 2 |
| 34 | 1 | 1 |
| 35 | 1 | 1 |
| 36 | 0.5 | 0.5 |
| 37 | 0.5 | 0.5 |
| 38 | 0.5 | 1 |
| 39 | 1 | 1 |
| 40 | 4 | 8 |
| 41 | 4 | 8 |
| 42 | 0.5 | 0.25 |
| 43 | 0.5 | 0.25 |
| 44 | 0.5 | 0.25 |
| 45 | 0.5 | 0.25 |
| 46 | 0.5 | 0.25 |
| 47 | 0.5 | 0.25 |
| 48 | 0.5 | 1 |
| 49 | 0.5 | 0.25 |
| 50 | 0.5 | 0.25 |
| 51 | 0.5 | 1 |
| 52 | 0.5 | 1 |
| 53 | 0.5 | 1 |
| 54 | 0.5 | 1 |
| 55 | 0.5 | 1 |
| 56 | 0.5 | 1 |
| 57 | 0.5 | 1 |
| 58 | 0.5 | 1 |
| 59 | 0.5 | 0.25 |
| 60 | 0.5 | 1 |
| 61 | 0.5 | 0.25 |
| 62 | 0.5 | 0.25 |
| 63 | 0.5 | 0.25 |
| 64 | 0.5 | 0.25 |

TABLE 2-continued

|         | Minimum Inhibitory Concentration ($MIC_{50}$, μg/ml) | |
| --- | --- | --- |
| Compound | MRSA | VRE |
| 65 | 0.5 | 0.25 |
| 66 | 0.5 | 0.25 |
| 67 | 0.5 | 0.25 |
| 68 | 0.5 | 0.25 |
| 69 | 0.5 | 0.25 |
| 70 | 0.5 | 0.25 |
| 71 | 0.5 | 0.125 |
| 72 | 32 | 32 |
| 73 | 32 | 32 |

NA: Not determined
MRSA: methicillin resistant *Staphylococcus aureus*
VRE: vancomycin resistant *Enterococci*

As illustrated in Table 2, the derivatives of the present invention had sufficient efficiency on antibacterial activity against *Staphylococcus aureus* (MRSA) and Enterococci (VRE) in spite of using lower concentration of the derivatives than that of the Zyvox. Accordingly, the compounds of the present invention may be useful as antibiotics.

(i) Experimental Example 2

Assay for Solubility

To test a solubility of the derivatives of the present invention, an experiment was carried out below. The derivatives of the present invention were added to 200 μl of distilled water and then the solution was stirred for 2 minutes. The turbidity of the solution was watched through naked eye.

When the derivatives were not dissolved completely, 50 μl of distilled water was added to the solution and then the turbidity of the solution was assayed in the above manner to find a point of becoming transparent solution.

When 2 mg of the derivatives was first added to distilled water and completely dissolved so that the solution became transparent, 2 mg of the derivatives was added more to the solution and then state of the solution was watched. The derivatives of the present invention were added to the five times and then solubility of the solution was assayed for. The assay for solubility was carried out the three times repeatedly in the above method and the results were averaged. The averages were shown in Table 3.

TABLE 3

| Compound | Solubility |
| --- | --- |
| Zyvox | 3 mg/ml |
| 10 | 10 μg/ml |
| 12 | 28 mg/ml |
| 16 | 20 μg/ml |
| 20 | 4.7 mg/ml |
| 27 | >50 mg/ml |
| 42 | >50 mg/ml |
| 43 | 4.2 mg/ml |
| 44 | >50 mg/ml |
| 45 | 12 mg/ml |
| 46 | <1.63 mg/ml |
| 47 | 2 mg/ml |
| 48 | >50 mg/ml |
| 49 | 2.6 mg/ml |
| 50 | 20.4 mg/ml |
| 51 | >50 mg/ml |
| 52 | >50 mg/ml |
| 53 | 30.3 mg/ml |

TABLE 3-continued

| Compound | Solubility |
| --- | --- |
| 54 | 2.9 mg/ml |
| 55 | 7.2 mg/ml |
| 56 | >50 mg/ml |
| 57 | >50 mg/ml |
| 58 | 5.5 mg/ml |
| 59 | >50 mg/ml |
| 60 | >50 mg/ml |
| 62 | 28 mg/ml |
| 64 | >50 mg/ml |
| 66 | 4.7 mg/ml |
| 68 | 2.6 mg/ml |
| 70 | >50 mg/ml |

As shown in table 3, the solubility of the compound 42 (>50 mg/ml) that is prodruged, of the derivatives was enhanced as compared with those of Zyvox (3 mg/ml) and the compound 10 (10 μg/ml).

Accordingly, when the derivatives of the present invention were formulated for oral administration, absorption of the derivatives may be enhanced. When the derivatives were formulated as injection, various formations of the derivatives may be obtained.

Experimental Example 3

Test of Acute Toxicity by Oral Administrating the Derivatives to Mouse

To test acute toxicity of the compounds of the present invention, the following experiment was carried out.

A mixture of 1% hydroxypropylmethylcellulose and 200 mg of one selected from the group consisting of the compounds 10, 12, 16, 17, 20, 22, 24 and 27 was administrated to 5 ICR mice (5-Week old males, 20 g±2 g by weight). And then lethality for 2 weeks, weight, symptoms etc. was watched to determine Minimum Lethal Dose (MLD, mg/kg). Zyvox of Pharmacia & Upjohn Inc was used as control. The results were represented in Table 4.

TABLE 4

| Compound | Minimum Lethal Dose (MLD, mg/kg) |
| --- | --- |
| Zyvox | >1000 |
| 10 | >1000 |
| 12 | >1000 |
| 16 | >1000 |
| 17 | >1000 |
| 20 | >1000 |
| 22 | >1000 |
| 24 | >1000 |
| 27 | >1000 |

Observation of survival, change in weight, tests in blood, and toxicity syndrome, etc. proved that administration of the composition of the present invention has no toxic effects The compounds of the present invention have excellent efficiency on antibacterial activity without any toxicity present according to Table 4.

Example Formulation

Preparation of Pharmaceutical Composition

Preparation as powder
Derivative of oxazolidinone 2 g
Lactose 1 g
The above materials were mixed and then the mixture was filled into a closed pack to prepare as powder.

Preparation as Tablet

Derivative of oxazolidinone 500 mg
Corn starch 100 mg
Lactose 100 mg
Magnesium stearate 2 mg The above materials were mixed and then the mixture was tabletted by the known method to prepare as tablet.

3. Preparation of Capsule
Derivative of oxazolidinone 500 mg
Corn starch 100 mg
Lactose 100 mg
Magnesium stearate 2 mg The above materials were mixed and the mixture was filled into gelatin capsule by the known method to prepare as capsule.

4. Preparation of Injection
Derivative of oxazolidinone 500 mg
Citrate buffer maintaining of pH 3.5
Dextrose isotonicity The derivative of oxazolidinone, salt of sodium citrate, citratic acid and dextrose were filled in 20 ml of vial, sterilized, for injection and then sealed off using aluminum cap. The mixture was dissolved in distilled water for injection and then diluted in distilled water solution, having appropriate volume, for injection.

What is claimed:

1. An oxazolidinone derivative of Formula (I), or a pharmaceutically acceptable salt thereof

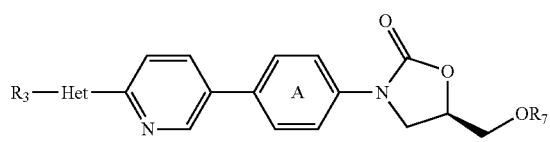

Formula (I)

wherein,
Het is selected from the group consisting of tetrazolyl and oxadiazolyl;
ring A is unsubstituted or has at least one fluorine substituent;
$R_7$ is
a) H, or
b) $PO(OH)_2$ or $PO(O)_2^{-2}(M^+)_2$, wherein $M^+$ is a pharmaceutically acceptable metal cation,
$R_3$ is hydrogen, $C_{1-4}$alkyl group that is unsubstituted, or substituted with cyano, —$(CH_2)$m-$OR_7$ or ketone; and
m is 0, 1, 2, 3, or 4.

2. The oxazolidinone derivative of claim 1
wherein $R_7$ is
b) $PO(OH)_2$ or $PO(O)_2^{-2}(M^+)_2$, wherein $M^+$ is a pharmaceutically acceptable metal cation, and
wherein the oxazolidinone derivative has a solubility of greater than 30 mg/mL.

3. The oxazolidinone derivative of claim 2
wherein the oxazolidinone derivative has a solubility of greater than 50 mg/mL.

4. The oxazolidinone derivative of claim 1,
wherein $R_7$ is $PO(OH)_2$ or $PO(O)_2^{-2}(M^+)_2$, wherein $M^+$ is a pharmaceutically acceptable metal cation.

5. The oxazolidinone derivative of claim 4,
wherein $M^+$ is $Na^+$.

6. The oxazolidinone derivative of claim 1
wherein $R_7$ is H.

7. The oxazolidinone derivative of claim 1
wherein Het is oxadiazolyl.

8. The oxazolidinone derivative of claim 1
wherein Het is tetrazolyl.

9. The oxazolidinone derivative of claim 8, which is

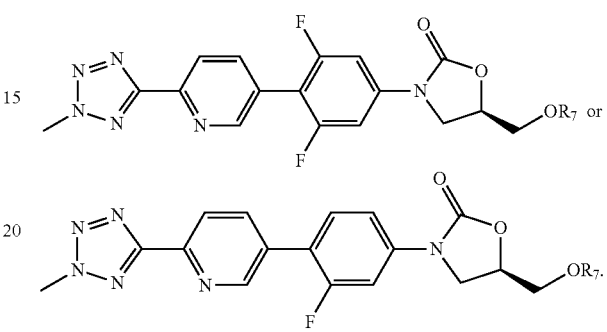

10. The oxazolidinone derivative of claim 4, which is

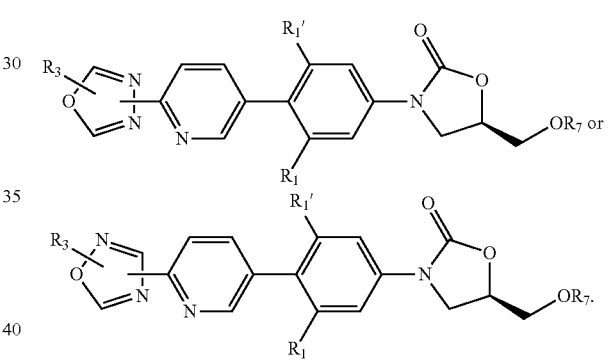

11. The oxazolidinone derivative of claim 10, wherein $R_1$ is hydrogen and $R'_1$ is fluorine.

12. The oxazolidinone derivative of claim 10 wherein $R_7$ is —H.

13. The oxazolidinone derivative of claim 10, wherein $R_7$ is selected from the group consisting of $PO(OH)_2$ and $PO(O)_2^-{}_2(M^+)_2$, wherein $M^+$ is a pharmaceutically acceptable metal cation.

14. The oxazolidinone derivative of claim 12, wherein $R_3$ is methyl.

15. The oxazolidinone derivative of claim 13, wherein $R_3$ is methyl.

16. The oxazolidinone derivative of claim 10, wherein the pharmaceutically acceptable salt is formed with an acid selected from the group consisting of hydrochloric acid, hydrobromic acid, sulfuric acid, phosphoric acid, citric acid, acetic acid, lactic acid, maleic acid, fumaric acid, gluconic acid, methane sulfonic acid, glyconic acid, succinic acid, 4-toluenesulfonic acid, trifluoroacetic acid, galacturonic acid, embonic acid, glutamic acid and aspartic acid.

17. The oxazolidinone derivative of claim 16, wherein the acid is hydrochloric acid or trifluoroacetic acid.

18. The oxazolidinone derivative of claim 10, having the structure

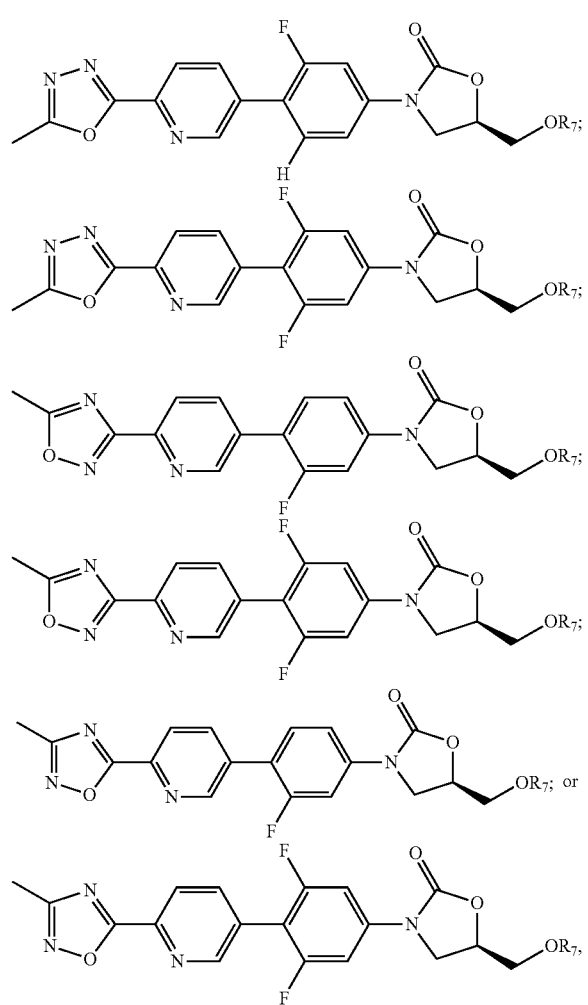

wherein $R_7$ is H, $PO(OH)_2$ or $PO(O)_2^{-2}(M^+)_2$, wherein $M^+$ is a pharmaceutically acceptable metal cation.

19. The oxazolidinone derivative of claim 18 wherein $M^+$ is $Na^+$.

20. A compound selected from the group consisting of

Compound 16) (R)-3-(4-(2-(2-methyl-[1,3,4]oxadiazol-5-yl)pyridin-5-yl)-3-fluorophenyl)-5-hydroxymethyl, Compound 27) (R)-3-(4-(2-(2-methyl-[1,3,4]oxadiazole-5-yl)pyridin-5-yl)-3-fluorophenyl)-5-glycyloxymethyl oxazolidin-2-one trifluoroacetic acid, Compound 39) (R)-3-(4-(2-(2-methyl-[1,3,4]oxadiazol-5-yl)pyridin-5-yl)-3,5-difluorophenyl)-5-hydroxymethyl oxazolidin-2-one, Compound 48) (R)-3-(4-(2-(2-methyl-[1,3,4]oxadiazol-5-yl)pyridin-5-yl)-3-fluorophenyl)-5-glycyloxymethyl oxazolidin-2-one hydrochloride, Compound 51) (R)-3-(4-(2-(2-methyl-[1,3,4]oxadiazol-5-yl)pyridin-5-yl)-3-fluorophenyl)-5-(L-alanyloxy)methyl oxazolidin-2-one trifluoroacetic acid, Compound 52) (R)-3-(4-(2-(2-methyl-[1,3,4]oxadiazol-5-yl)pyridin-5-yl)-3-fluorophenyl)-5-(L-alanyloxy)methyl oxazolidin-2-one hydrochloride, Compound 53) (R)-3-(4-(2-(2-methyl-[1,3,4]oxadiazol-5-yl)pyridin-5-yl)-3-fluorophenyl)-5-(L-valyloxy)methyl oxazolidin-2-one trifluoroacetic acid, Compound 54) (R)-3-(4-(2-(2-methyl-[1,3,4]oxadiazol-5-yl)pyridin-5-yl)-3-fluorophenyl)-5-(L-valyloxy)methyl oxazolidin-2-one hydrochloride, Compound 55) (R)-3-(4-(2-(2-methyl-[1,3,4]oxadiazol-5-yl)pyridin-5-yl)-3-fluorophenyl)-5-(L-prolinyloxy)methyl oxazolidin-2-one trifluoroacetic acid, Compound 56) (R)-3-(4-(2-(2-methyl-[1,3,4]oxadiazol-5-yl)pyridin-5-yl)-3-fluorophenyl)-5-(L-prolinyloxy)methyl oxazolidin-2-one hydrochloride, Compound 57) (R)-3-(4-(2-(2-methyl-[1,3,4]oxadiazol-5-yl)pyridin-5-yl)-3-fluorophenyl)-5-(β-alanyloxy)methyl oxazolidin-2-one trifluoroacetic acid, Compound 58) (R)-3-(4-(2-(2-methyl-[1,3,4]oxadiazol-5-yl)pyridin-5-yl)-3-fluorophenyl)-5-(β-alanyloxy)methyl oxazolidin-2-one hydrochloride, and Compound 60) (R)-[3-(4-(2-(2-methyl-[1,3,4]oxadiazol-5-yl)pyridin-5-yl)-3-fluorophenyl)-2-oxo-5-oxazolidinyl]methyl disodiumphosphate.

21. A pharmaceutical composition comprising the oxazolidinone derivative of claim 1 and a pharmaceutically acceptable carrier.

22. A pharmaceutical composition of claim 21, wherein the pharmaceutical composition is an injectable composition.

23. A method of treating a bacterial infection in a subject, comprising administering to the subject an effective amount of the oxazolidinone derivative of claim 1.

24. The method of claim 23, wherein the bacterial infection results from a Gram-positive bacterium.

25. The method of claim 24, wherein the Gram-positive bacterium is selected from the group consisting of *Staphylococcus, Enterococcus, Streptococcus, Bacteroides, Clostridium*, and *Mycobacterium*.

26. The method of claim 25, wherein the bacterium is selected from the group consisting of *Staphylococcus, Enterococcus*, and *Streptococcus*.

27. The oxazolidinone derivative of claim 8, wherein $R_1$ is hydrogen and $R'_1$ is fluorine.

28. The oxazolidinone derivative of claim 8 wherein $R_7$ is —H.

29. The oxazolidinone derivative of claim 8, wherein $R_7$ is $PO(OH)_2$ or $PO(O)_2^{-2}(M^+)_2$, wherein $M^+$ is a pharmaceutically acceptable metal cation.

30. The oxazolidinone derivative of claim 28, wherein $R_3$ is methyl.

31. The oxazolidinone derivative of claim 29, wherein $R_3$ is methyl.

32. The oxazolidinone derivative of claim 8, wherein the pharmaceutically acceptable salt is formed with an acid selected from the group consisting of hydrochloric acid, hydrobromic acid, sulfuric acid, phosphoric acid, citric acid, acetic acid, lactic acid, maleic acid, fumaric acid, gluconic acid, methane sulfonic acid, glyconic acid, succinic acid, 4-toluenesulfonic acid, trifluoroacetic acid, galacturonic acid, embonic acid, glutamic acid and aspartic acid.

33. The oxazolidinone derivative of claim 32, wherein the acid is hydrochloric acid or trifluoroacetic acid.

* * * * *

UNITED STATES PATENT AND TRADEMARK OFFICE
CERTIFICATE OF CORRECTION

PATENT NO. : 8,420,676 B2
APPLICATION NO. : 12/211655
DATED : April 16, 2013
INVENTOR(S) : Rhee et al.

It is certified that error appears in the above-identified patent and that said Letters Patent is hereby corrected as shown below:

In the Specification

In column 3 at line 41, Change "galuturonic acid," to --galacturonic acid--.

In column 3 at line 46, Change "4-glycyloxymethylpylolidin" to --4-glycyloxymethylpyrrolidin--.

In column 4 at line 40, Change "4,5-dihydroxazole" to --4,5-dihydrooxazole--.

In column 26 at lines 40-45, Change " 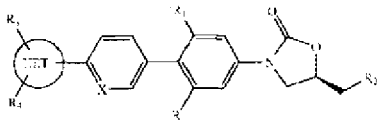 " to 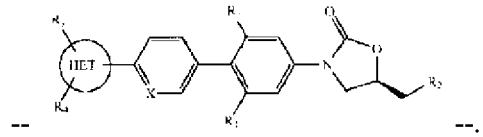 -- --.

In column 27 at line 1, Change "(H)" to --(II)--.

In column 27 at line 4, Change "anilin" to --aniline--.

In column 27 at line 8, Change "n-butyllitium, sec-butyllitium," to --n-butyllithium, sec-butyllithium,--.

In column 27 at lines 8-9, Change "tert-butyllitium," to --tert-butyllithium--.

In column 27 at line 9, Change "n-butyllitium." to --n-butyllithium.--.

In column 27 at line 19, Change "the" to --to the--.

In column 27 at line 27, Change "1-methyl-2-pyrolidone," to --1-methyl-2-pyrrolidone,--.

In column 27 at line 34, Change "1-methyl-2-pyrolidone," to --1-methyl-2-pyrrolidone,--.

In column 27 at lines 42-43, Change "1-methyl-2-pyrolidone," to --1-methyl-2-pyrrolidone,--.

In column 27 at line 65, Change "hours," to --hours--.

Signed and Sealed this
Eighth Day of April, 2014

Michelle K. Lee
*Deputy Director of the United States Patent and Trademark Office*

In column 32 at line 17, Change "(4-tributhylstannyl)" to --(4-tributylstannyl)--.

In column 32 at line 62, Change "dimethyloxzol" to --dimethyloxazol--.

In column 34 at line 28, Change "hours." to --10 hours.--.

In column 34 at line 47, Change "(compound" to --(compound 20)--.

In column 34 at line 50, Change "Example" to --Example 10--.

In column 34 at line 63, Change "Example" to --Example 10--.

In column 35 at line 8, Change "Example" to --Example 10--.

In column 35 at line 21, Change "Example" to --Example 10--.

In column 35 at line 31, Change "(compound" to --(compound 34)--.

In column 35 at line 34, Change "Example" to --Example 10--.

In column 35 at line 46, Change "Example" to --Example 10--.

In column 37 at line 22, Change "7.47(d, 1H)" to --7.47(d,1H),--.

In column 37 at line 38, Change "7.44(d, 1H)" to --7.44(d,1H),--.

In column 38 at line 37, Change "7.59(dd, 1H)" to --7.59(dd,1H),--.

In column 38 at line 41, Change "7.59(dd, 1H)" to --7.59(dd,1H),--.

In column 38 at line 55, Change "7.61(dd, 1H)" to --7.61(dd,1H),--.

In column 39 at line 3, Change "7.60(dd, 1H)" to --7.60(dd,1H),--.

In column 39 at line 14, Change "floride" to --fluoride--.

In column 39 at line 19, Change "7.66(dd, 1H)" to --7.66(dd,1H),--.

In column 41 at line 32, Change "methansulfonyloxymethyl" to --methanesulfonyloxymethyl--.

In column 43 at line 60, Delete "47)" and insert the same on Col. 43, Line 57 as a continuation of paragraph.

In column 46 at line 58, Change "ditetrabuthylester" to --ditetrabutylester--.

In column 49 at line 59, Change "7.59(dd, 1H)" to --7.59(dd,1H),--.

In column 52 at line 54, Change "effects" to --effects.--.

In column 53 at line 23, Change "citratic" to --citric--.

In the Claims

In column 54 at line 26, In Claim 10, Change "claim 4," to --claim 8,--.